(12) United States Patent
Barascud et al.

(10) Patent No.: US 12,422,927 B2
(45) Date of Patent: Sep. 23, 2025

(54) BRAIN-COMPUTER INTERFACE

(71) Applicant: NextMind SAS, Paris (FR)

(72) Inventors: Nicolas Barascud, Paris (FR); Nelson Steinmetz, Paris (FR); Robin Zerafa, Paris (FR); Sid Kouider, Paris (FR)

(73) Assignee: NextMind SAS, Paris (FR)

( * ) Notice: Subject to any disclaimer, the term of this patent is extended or adjusted under 35 U.S.C. 154(b) by 0 days.

(21) Appl. No.: 17/786,437

(22) PCT Filed: Nov. 6, 2020

(86) PCT No.: PCT/EP2020/081338
§ 371 (c)(1),
(2) Date: Jun. 16, 2022

(87) PCT Pub. No.: WO2021/121766
PCT Pub. Date: Jun. 24, 2021

(65) Prior Publication Data
US 2023/0359275 A1 Nov. 9, 2023

Related U.S. Application Data

(60) Provisional application No. 62/949,803, filed on Dec. 18, 2019.

(51) Int. Cl.
G06F 3/01 (2006.01)

(52) U.S. Cl.
CPC .................................. G06F 3/015 (2013.01)

(58) Field of Classification Search
CPC ........ G06F 3/015; G06F 3/013; G06F 3/0219; G06F 3/0236; G06F 3/04842;
(Continued)

(56) References Cited

U.S. PATENT DOCUMENTS 10,042,421 B2   8/2018   Mitchell et al.
2016/0262608 A1 9/2016   Krueger
(Continued)

FOREIGN PATENT DOCUMENTS

CN   103631941 A   3/2014
CN   103699230 A   4/2014
(Continued)

OTHER PUBLICATIONS

"International Application Serial No. PCT/EP2020/081338, International Search Report mailed Feb. 18, 2021", 5 pgs.
(Continued)

Primary Examiner — Robin J Mishler
(74) Attorney, Agent, or Firm — Schwegman Lundberg & Woessner, P.A.

(57) ABSTRACT

A system and method relating to a brain-computer interface in which a visual stimulus overlaying one or more objects is provided, at least a portion of the visual stimulus having a characteristic modulation. The brain computer interface measures neural response to objects viewed by a user. The neural response to the visual stimulus is correlated to the modulation, the correlation being stronger when attention is
(Continued)

concentrated upon the visual stimulus. The visual stimulus includes a feedback element that varies according to a measure of attention on the or each overlaid object.

13 Claims, 14 Drawing Sheets

(58) Field of Classification Search
CPC .......... G06F 18/214; G06F 2203/0381; G06F 2218/02; G06F 2218/12; G06F 3/017; G06F 3/0346; G06F 3/038; A61B 5/16; A61B 5/163; A61B 5/333; A61B 5/369; A61B 5/378; A61B 5/7264; A61B 5/7435; A61B 5/7475

See application file for complete search history.

(56) References Cited

U.S. PATENT DOCUMENTS

| | | | |
|---|---|---|---|
| 2018/0253144 A1 | 9/2018 | Alleaume et al. | |
| 2019/0307356 A1 | 10/2019 | Sarma et al. | |
| 2020/0337653 A1* | 10/2020 | Alcaide | A61B 5/369 |

FOREIGN PATENT DOCUMENTS

| | | |
|---|---|---|
| CN | 106455968 A | 2/2017 |
| CN | 106990834 A | 7/2017 |
| CN | 114830069 A | 7/2022 |
| EP | 3154000 A2 | 4/2017 |
| WO | WO-2019048525 A1 | 3/2019 |
| WO | WO-2019144019 A1 | 7/2019 |
| WO | WO-2021121766 A1 | 6/2021 |

OTHER PUBLICATIONS

"International Application Serial No. PCT/EP2020/081338, Written Opinion mailed Feb, 18, 2021", 9 pgs.

Erwei, Yin, et al., "A Dynamically Optimized SSVEP Brain-Computer Interface (BCI) Spe", IEEE Transactions on Biomedical Engineering, IEEE Service Center, Piscataway, NJ, USA, vol. 62, No. 6, (Jun. 1, 2015), 1447-1456.

"European Application Serial No. 20803549.3, Response filed Jan. 24, 2023 Communication pursuant to Rules 161(1) and 162 EPC mailed Jul. 26, 2022", 26 pgs.

"Chinese Application Serial No. 202080088687.2, Office Action mailed Aug. 26, 2024", w/ English Translation, 14 pgs.

"Korean Application Serial No. 10-2022-7024105, Notice of Preliminary Rejection mailed Oct. 29, 2024", w/ English translation, 17 pgs.

"Chinese Application Serial No. 202080088687.2, Response filed Dec. 5, 2024 to Office Action mailed Aug. 26, 2024", w/ English Claims, 59 pgs.

"European Application Serial No. 20803549.3, Communication Pursuant to Article 94(3) EPC mailed Dec. 20, 2024", 5 pgs.

"European Application Serial No. 20803549.3, Response filed Mar. 28, 2025 to Communication Pursuant to Article 94(3) EPC mailed Dec. 20, 2024", 9 pgs.

"Korean Application Serial No. 10-2022-7024105, Response filed Dec. 23, 2024 to Notice of Preliminary Rejection mailed Oct. 29, 2024", w/ current English claims, 25 pgs.

"Korean Application Serial No. 10-2022-7024105, Notice of Preliminary Rejection mailed May 20, 2025", w/ English Translation, 17 pgs.

* cited by examiner (b)

(c)

BRAIN-COMPUTER INTERFACE

CROSS-REFERENCE TO RELATED APPLICATIONS

This application is a U.S. national-phase application filed under 35 U.S.C. § 371 from International Application Serial No. PCT/EP2020/081338, filed Nov. 6, 2020, and published as WO 2021/121766 on Jun. 24, 2021, which claims the benefit of priority of U.S. Provisional Application Ser. No. 62/949,803, filed Dec. 18, 2019, each of which are incorporated by reference herein in their entireties.

TECHNICAL FIELD OF THE INVENTION

Embodiments of the present disclosure relate to the operation of brain-computer interfaces involving visual sensing and in particular feedback interaction through such interfaces.

STATE OF THE ART

In visual brain-computer interfaces (BCIs), neural responses to a target stimulus, generally among a plurality of generated visual stimuli presented to the user, are used to infer (or "decode") which stimulus is essentially the object of focus at any given time. The object of focus can then be associated with a user-selectable or -controllable action.

Neural responses may be obtained using a variety of known techniques. One convenient method relies upon surface electroencephalography (EEG), which is non-invasive, has fine-grained temporal resolution and is based on well-understood empirical foundations. Surface EEG makes it possible to measure the variations of diffuse electric potentials on the surface of the skull (i.e. the scalp) of a subject in real-time. These variations of electrical potentials are commonly referred to as electroencephalographic signals or EEG signals.

In a typical BCI, visual stimuli are presented in a display generated by a display device. Examples of suitable display devices (some of which are illustrated in FIG. 9) include television screens & computer monitors 902, projectors 910, virtual reality headsets 906, interactive whiteboards, and the display screen of tablets 904, smartphones, smart glasses 908, etc. The visual stimuli 911, 911', 912, 912', 914, 914', 916 may form part of a generated graphical user interface (GUI) or they may be presented as augmented reality (AR) or mixed reality graphical objects 916 overlaying a base image: this base image may simply be the actual field of view of the user (as in the case of a mixed reality display function projected onto the otherwise transparent display of a set of smart glasses) or a digital image corresponding to the user's field of view but captured in real-time by an optical capture device (which may in turn capture an image corresponding to the user's field of view amongst other possible views).

Inferring which of a plurality of visual stimuli (if any) is the object of focus at any given time is fraught with difficulty. For example, when a user is facing multiple stimuli, such as for instance the digits displayed on an on-screen keypad, it has proven nearly impossible to infer which one is under focus directly from brain activity at a given time. The user perceives the digit under focus, say digit 5, so the brain must contain information that distinguishes that digit from others, but current methods are unable to extract that information. That is, current methods can, with difficulty, infer that a stimulus has been perceived, but they cannot determine which specific stimulus is under focus using brain activity alone.

To overcome this issue and to provide sufficient contrast between stimulus and background (and between stimuli), it is known to configure the stimuli used by visual BCIs to blink or pulse (e.g. large surfaces of pixels switching from black to white and vice-versa), so that each stimulus has a distinguishable characteristic profile over time. The flickering stimuli give rise to measurable electrical responses. Specific techniques monitor different electrical responses, for example steady state visual evoked potentials (SSVEPs) and P-300 event-related potentials. In typical implementations, the stimuli flicker at a rate exceeding 6 Hz. As a result, such visual BCIs rely on an approach that consists of displaying the various stimuli discretely, rather than constantly, and typically at different points in time. Brain activity associated with attention focused on a given stimulus is found to correspond (i.e. correlate) with one or more aspect of the temporal profile of that stimulus, for instance the frequency of the stimulus blink and/or the duty cycle over which the stimulus alternates between a blinking state and a quiescent state.

Thus, decoding of neural signals relies on the fact that when a stimulus is turned on, it will trigger a characteristic pattern of neural responses in the brain that can be determined from electrical signals, i.e. the SSVEPs or P-300 potentials, picked up by electrodes of an EEG device, the electrodes of an EEG helmet, for example. This neural data pattern might be very similar or even identical for the various digits, but it is time-locked to the digit being perceived: only one digit may pulse at any one time so that the correlation with a pulsed neural response and a time at which that digit pulses may be determined as an indication that that digit is the object of focus.

By displaying each digit at different points in time, turning that digit on and off at different rates, applying different duty cycles, and/or simply applying the stimulus at different points in time, the BCI algorithm can establish which stimulus, when turned on, is most likely to be triggering a given neural response, thereby allowing a system to determine the target under focus.

Visual BCIs have improved significantly in recent years, so that real-time and accurate decoding of the user's focus is becoming increasingly practical. Nevertheless, the constant blinking of the stimuli, sometimes all over the screen when there are many of them, is an intrinsic limitation for a large-scale use of this technology. Indeed, it can cause discomfort and mental fatigue, and, if sustained, physiological responses such as headaches. In addition, the blinking effect can impede the ability of the user to focus on a specific target, and the system to determine the object of focus quickly and accurately.

For instance, when a user of the on-screen keypad discussed above tries to focus on digit 5, the other (i.e., peripheral) digits act as distractors, their presence and the fact that they are exhibiting a blinking effect drawing the user's attention momentarily. The display of the peripheral digits induces interference in the user's visual system. This interference in turn impedes the performance of the BCI.

Consequently, there is a need for an improved method for differentiating between screen targets and their display stimuli in order to determine which one a user is focusing on and for discriminating the object of focus (the target) from the objects peripheral to the target (the distractors) with speed and accuracy.

It is therefore desirable to provide brain-computer interfaces that address the above challenges.

SUMMARY

The present disclosure relates to a brain-computer interface in which visual stimuli are presented on a graphical interface such that they are neurally decodable and offer an improved user experience.

The present disclosure further relates to a brain-computer interface (BCI) in which a visual stimulus overlaying one or more objects includes a respective feedback element that varies according to a measure of attention on the or each object. The visual stimulus is generated by a stimulus generator and typically presented on a screen or other display device.

At least a portion of the visual stimulus has a characteristic modulation. Neural responses to the objects in the user's field of view are captured by a neural signal capture device in the BCI. The user's neural response to the viewed objects may in turn be measured and decoded to determine which object of interest is the focus of the user's attention and the current level of attention the user is giving to that object, the neural response being stronger when attention is concentrated upon the visual stimulus.

The variation of the feedback element is arranged to be linked to the strength of neural response. Thus, the feedback element of the visual stimulus may change visual form (so that the user sees an effect upon the feedback element that corresponds to their attention level). Furthermore, the user is provided with a target for that attention and may adapt their behavior to enhance the visual effect (effectively learning how to operate the BCI more efficiently). In other words, the user sees an effect upon the feedback element that they are causing via the BCI and may learn to focus attention using the BCI by seeking to observe the effect alter. In addition, the appearance of the visual effect associated with the focused attention serves to validate the selection of the underlying object.

In certain embodiments, the feedback element represents degree of attention from absence of attention to a focused level of attention as progressive step-wise or continuous changes between an orderless (e.g. pseudo-random) distribution of visual elements to a completely ordered distribution (e.g. to a recognizable shape, character or symbol such as a reticule, target mark or cross-hair).

In certain embodiments, the entire visual stimulus is a feedback element. In other embodiments the visual stimulus further includes a background element in addition to the feedback element. In certain embodiments, the background element has the characteristic temporal modulation of the visual stimulus (i.e. the decodable modulation), while the feedback element is not modulated. In certain embodiments, the feedback element has the characteristic modulation of the visual stimulus, while the background element is not modulated.

In certain embodiments, the characteristic modulation of the visual stimulus is applied to both background and feedback element. The magnitude of the modulation in background and feedback element may differ.

In certain aspects, the present disclosure describes a system and method for improving the accuracy and speed of determining the object of focus in a field of objects, or as a specific area in a single, large target. Image data for all objects are processed to extract a version composed of only high spatial frequency (HSF) components for each object.

The present disclosure relates to techniques for taking objects of (potential) interest within the field of view of a user (typically, but not always on a display presented to the user), extracting components that relate to visual properties of those objects (for example their edges), and applying a modulation to the high spatial frequency component of those visual properties. Thus, a blinking visual stimulus used to elicit neural responses, such as visual evoked potentials (VEPs), may be conveyed only through the HSF version of the objects. The modulation makes the object blink or otherwise visually alter so that the modulation acts as a stimulus for a correlated neural response. The neural response may in turn be measured and decoded to determine which object of interest is the focus of the user's attention.

In certain aspects, the image data may further be processed to extract a further version of the object composed only of the low spatial frequency (LSF) components. Where an LSF version is extracted, the modulated HSF version may be superimposed on the LSF version (which does not blink).

In one aspect, the present disclosure comprises a closed-loop feedback system wherein a user peers at a screen and its objects, neural activity is captured as signals using a helmet of electrodes, and the proportions of HSF detected from neural activity, and associated with each object, will vary as the user's object of focus changes. This is somewhat equivalent to blinking the objects at different rates and duty cycles but presents far less interference because of the filtering such that blinking display objects are those which evoke essentially HSF responses (e.g. HSF versions). If the object is peripheral, the blinking of its HSF version is naturally subdued by the human visual behavior. However, an object of focus, with its HSF version blinking, will evoke a readily identifiable neural response. As a result, interference is significantly quashed making the experience more comfortable and the identification of an object of focus both more accurate and timely.

In each of the embodiments above, the modulation may be applied preferentially or exclusively to a high spatial frequency component of the projected overlay image (i.e. the background and/or feedback element).

According to a further aspect, the present disclosure relates to a brain computer interface system, comprising: a display unit for displaying image data, the image data including at least one object, the display unit further outputting a respective visual stimulus to correspond to one or more of said objects, a stimulus generator for generating the or each visual stimulus with a corresponding characteristic modulation; a neural signal capture device configured to capture neural signals associated with a user; and an interfacing device operatively coupled to the neural signal capture device and the stimulus generator, the interfacing device being configured to: receive the neural signals from the neural signal capture device; determine a strength of components of the neural signals having a property associated with the respective characteristic modulations of the or each visual stimulus; determine which of the at least one visual stimuli is associated with an object of focus of the user based on the neural signals, the object of focus being inferred from the presence and/or relative strength of the components of the neural signals having a property associated with the characteristic modulation of the visual stimulus; and cause the stimulus generator to generate the visual stimulus for the object of focus with a feedback element, the feedback element being displayed with an effect that varies in accordance with the determined strength of the component having a property associated with the characteristic modulations of the visual stimulus for the object of focus.

According to another aspect, the present disclosure relates to a method of operation of a brain computer interface system, the brain computer interface system including a display unit, a stimulus generator and a neural signal capture device, the display unit displaying image data including at least one object and outputting a visual stimulus to correspond to one or more of said objects, the visual stimulus having a characteristic modulation, wherein the method comprises, in a hardware interfacing device operatively coupled to the neural signal capture device and the stimulus generator: receiving the neural signals from the neural signal capture device; determining a strength of components of the neural signals having a property associated with the respective characteristic modulations of the or each visual stimulus; determining which of the at least one visual stimuli is associated with an object of focus of the user based on the neural signals, the object of focus being inferred from the presence and/or relative strength of the components of the neural signals having a property associated with the characteristic modulation of the visual stimulus; and causing the stimulus generator to generate the visual stimulus for the object of focus with a feedback element, the feedback element being displayed with an effect that varies in accordance with the determined strength of the component having a property associated with the characteristic modulations of the visual stimulus for the object of focus.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Figure 1:
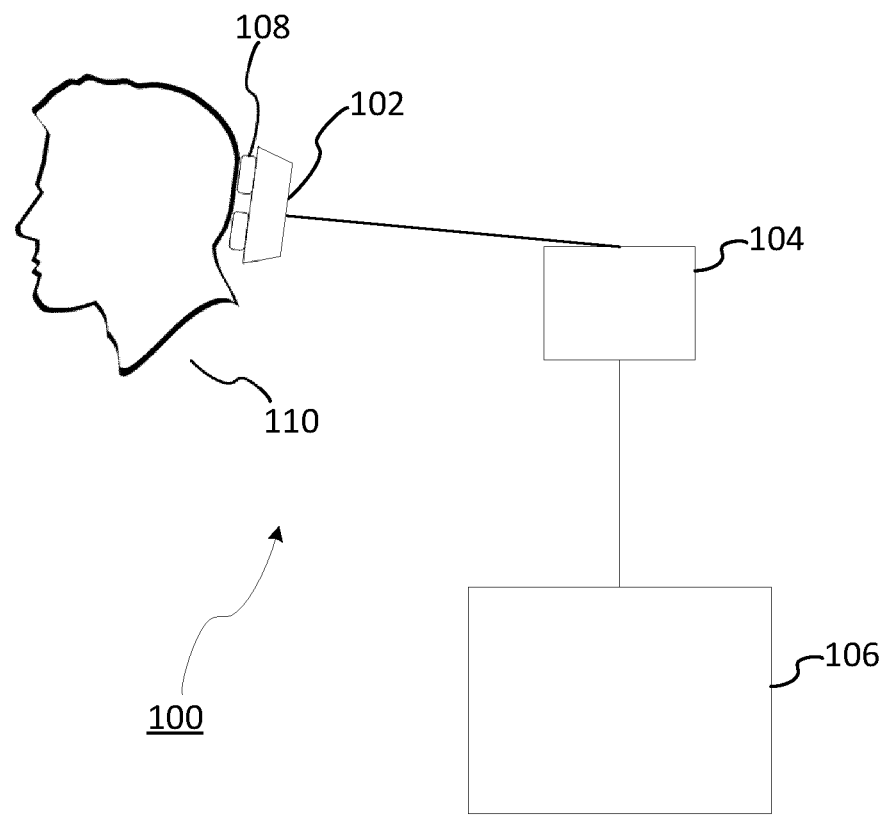
FIG. 1 illustrates an electronic architecture for receiving and processing EEG signals according to the present disclosure.

FIG. 1 illustrates an example of an electronic architecture for the reception and processing of EEG signals by means of an EEG device 100 according to the present disclosure.

To measure diffuse electric potentials on the surface of the skull of a subject 110, the EEG device 100 includes a portable device 102 (i.e. a cap or headpiece), analog-digital conversion (ADC) circuitry 104 and a microcontroller 106. The portable device 102 of FIG. 1 includes one or more electrodes 108, typically between 1 and 128 electrodes, advantageously between 2 and 64, advantageously between 4 and 16.

Each electrode 108 may comprise a sensor for detecting the electrical signals generated by the neuronal activity of the subject and an electronic circuit for pre-processing (e.g. filtering and/or amplifying) the detected signal before analog-digital conversion: such electrodes being termed "active". The active electrodes 108 are shown in use in FIG. 1, where the sensor is in physical contact with the subject's scalp. The electrodes may be suitable for use with a conductive gel or other conductive liquid (termed "wet" electrodes) or without such liquids (i.e. "dry" electrodes).

Each ADC circuit 104 is configured to convert the signals of a given number of active electrodes 108, for example between 1 and 128.

The ADC circuits 104 are controlled by the microcontroller 106 and communicate with it for example by the protocol SPI ("Serial Peripheral Interface"). The microcontroller 106 packages the received data for transmission to an external processing unit (not shown), for example a computer, a mobile phone, a virtual reality headset, an automotive or aeronautical computer system, for example a car computer or a computer system, airplane, for example by Bluetooth, Wi-Fi ("Wireless Fidelity") or Li-Fi ("Light Fidelity").

In certain embodiments, each active electrode 108 is powered by a battery (not shown in FIG. 1). The battery is conveniently provided in a housing of the portable device 102.

In certain embodiments, each active electrode 108 measures a respective electric potential value from which the potential measured by a reference electrode (Ei=Vi−Vref) is subtracted, and this difference value is digitized by means of the ADC circuit 104 then transmitted by the microcontroller 106.

In certain embodiments, the method of the present disclosure introduces target objects for display in a graphical user interface of a display device. The target objects include control items and the control items are in turn associated with user-selectable actions.

Figure 2:
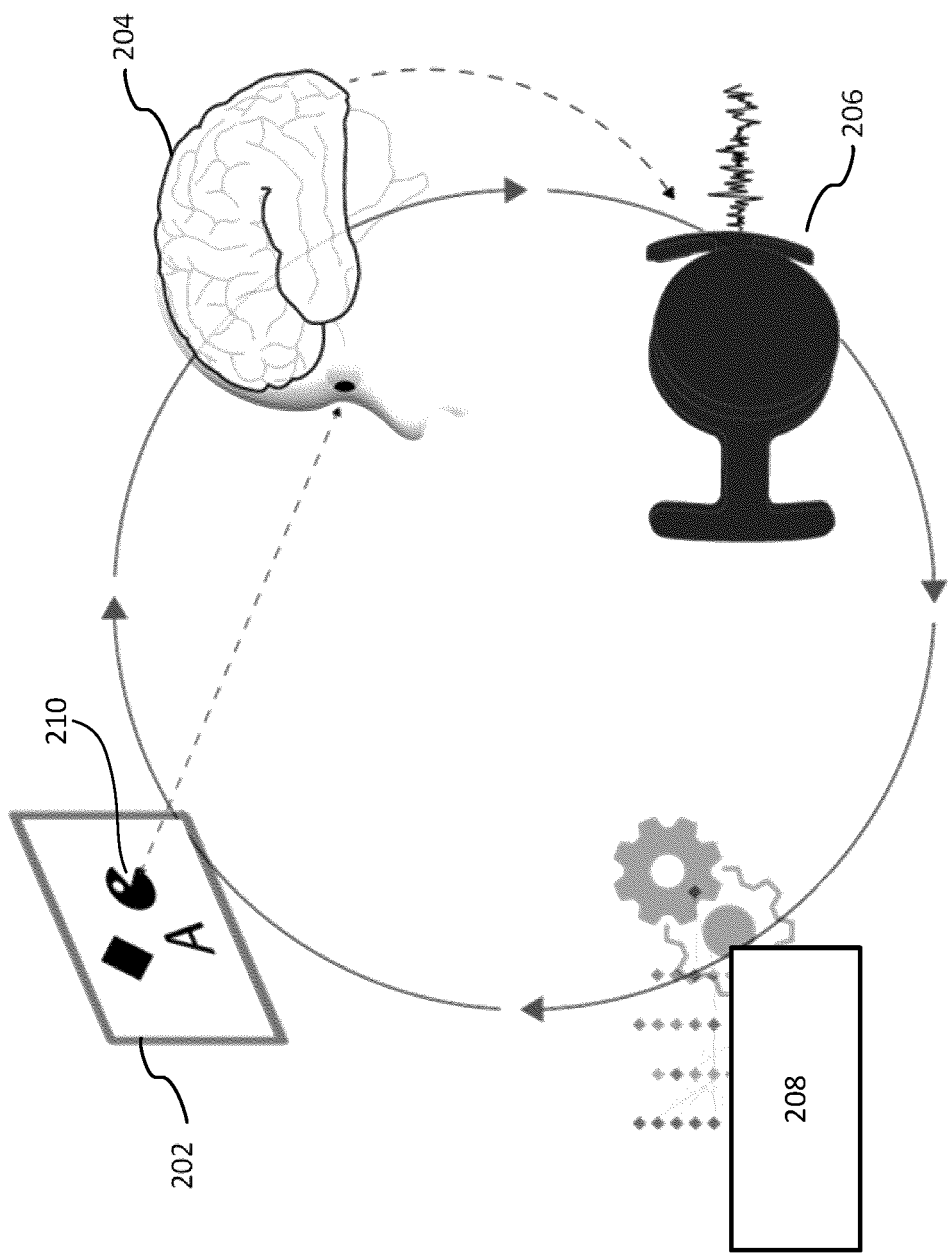
FIG. 2 illustrates a system incorporating a brain computer interface (BCI) according to the present disclosure.

FIG. 2 illustrates a system incorporating a brain computer interface (BCI) according to the present disclosure. The system incorporates a neural response device 206, such as the EEG device 100 illustrated in FIG. 1. In the system, an image is displayed on a display of a display device 202. The subject 204 views the image on the display, focusing on a target object 210.

Figure 3A:
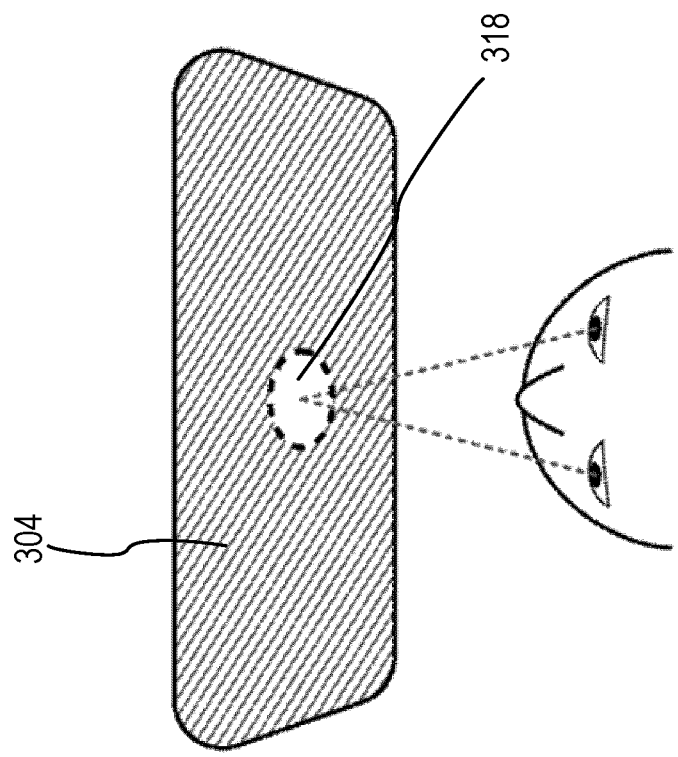
FIGS. 3A to 3C illustrate the display of target objects having respective, distinct varying temporal characteristics according to the present disclosure.
Figure 3A:
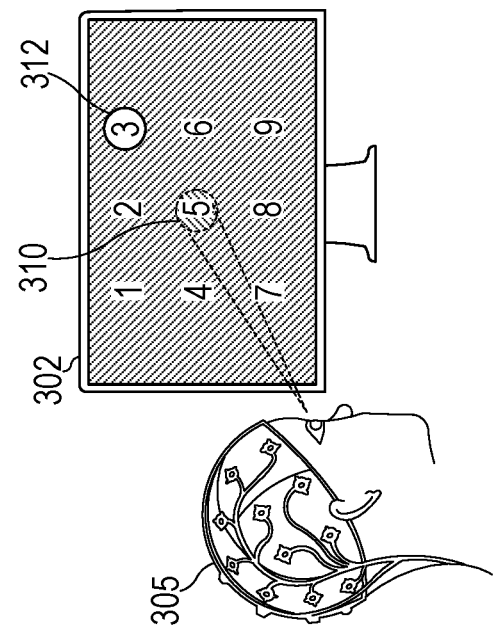
Figure 3B:
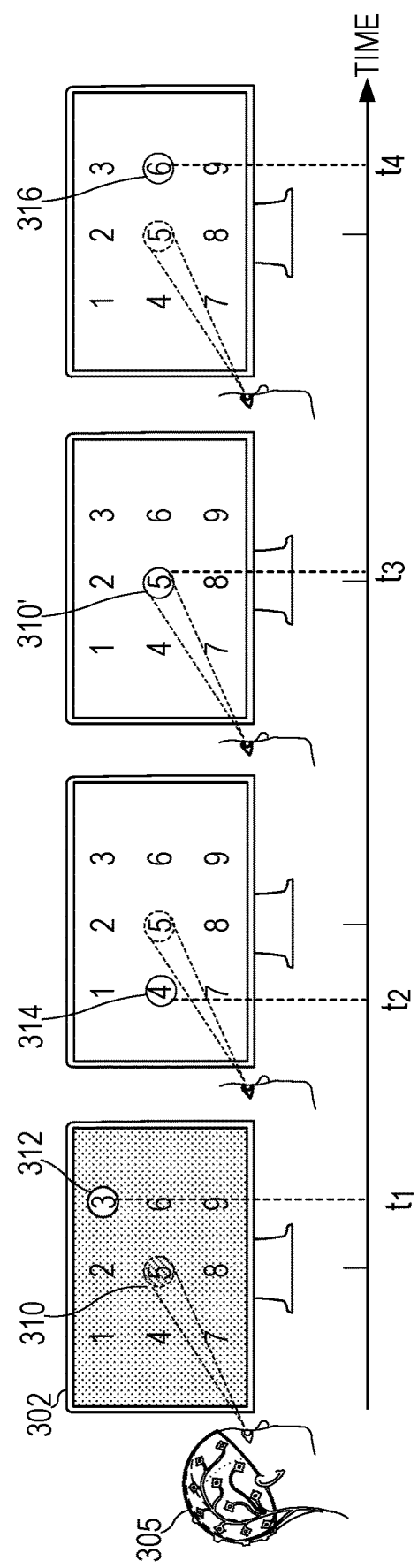
Figure 3C:
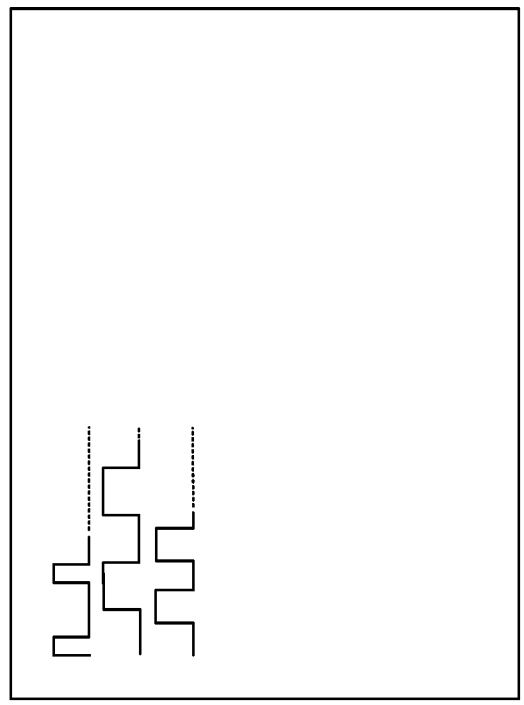

In an embodiment, the display device 202 displays at least the target object 210 as a graphical object with a varying temporal characteristic distinct from the temporal characteristic of other displayed objects and/or the background in the display. The varying temporal characteristic may be, for example, a constant or time-locked flickering effect altering the appearance of the target object at a rate greater than 6 Hz. In another embodiment, the varying temporal characteristic may use a pseudo-random temporal code so that a flickering effect is generated that alters the appearance of the target object a few times a second on average, for example at a rate that is on average 3 Hz. Where more than one graphical object is a potential target object (i.e. where the viewing subject is offered a choice of target object to focus attention on), each object is associated with a discrete spatial and/or temporal code. FIGS. 3A to 3C illustrate the display of target objects having respective, distinct varying temporal characteristics.

The neural response device 206 detects neural responses (i.e. tiny electrical potentials indicative of brain activity in the visual cortex) associated with attention focused on the target object; the visual perception of the varying temporal characteristic of the target object(s) therefore acts as a stimulus in the subject's brain, generating a specific brain response that accords with the code associated with the target object in attention. The detected neural responses (e.g. electrical potentials) are then converted into digital signals and transferred to a processing device 208 for decoding. Examples of neural responses include visual evoked potentials (VEPs), which are commonly used in neuroscience research. The term VEPs encompasses conventional SSVEPs, as mentioned above, where stimuli oscillate at a specific frequency and other methods such as the code-modulated VEP, stimuli are subject to a variable or pseudo-random temporal code. The sympathetic neural response, where the brain appears to "oscillate" or respond in synchrony with the flickering temporal characteristic is referred to herein as "neurosynchrony".

The processing device 208 executes instructions that interpret the received neural signals to determine feedback indicating the target object having the current focus of (visual) attention in real-time. Decoding the information in the neural response signals relies upon a correspondence between that information and one or more aspect of the temporal profile of the target object (i.e. the stimulus). In certain embodiments, the processing device 208 and neural response device 206 may be provided in a single device so that decoding algorithms are executed directly on the detected neural responses. Thus, BCIs making use of visually associated neural signals can be used to determine which objects on a screen a user is focusing on.

In certain embodiments, the processing device may conveniently generate the image data presented on the display device 202 including the temporally varying target object.

In certain embodiments, the display device 202 displays an overlay object as a graphical object with a varying temporal characteristic distinct from the temporal characteristic of other displayed objects and/or the background in the display, the overlay object is then displayed as a graphical layer over at least an identified target object.

Figure 4:
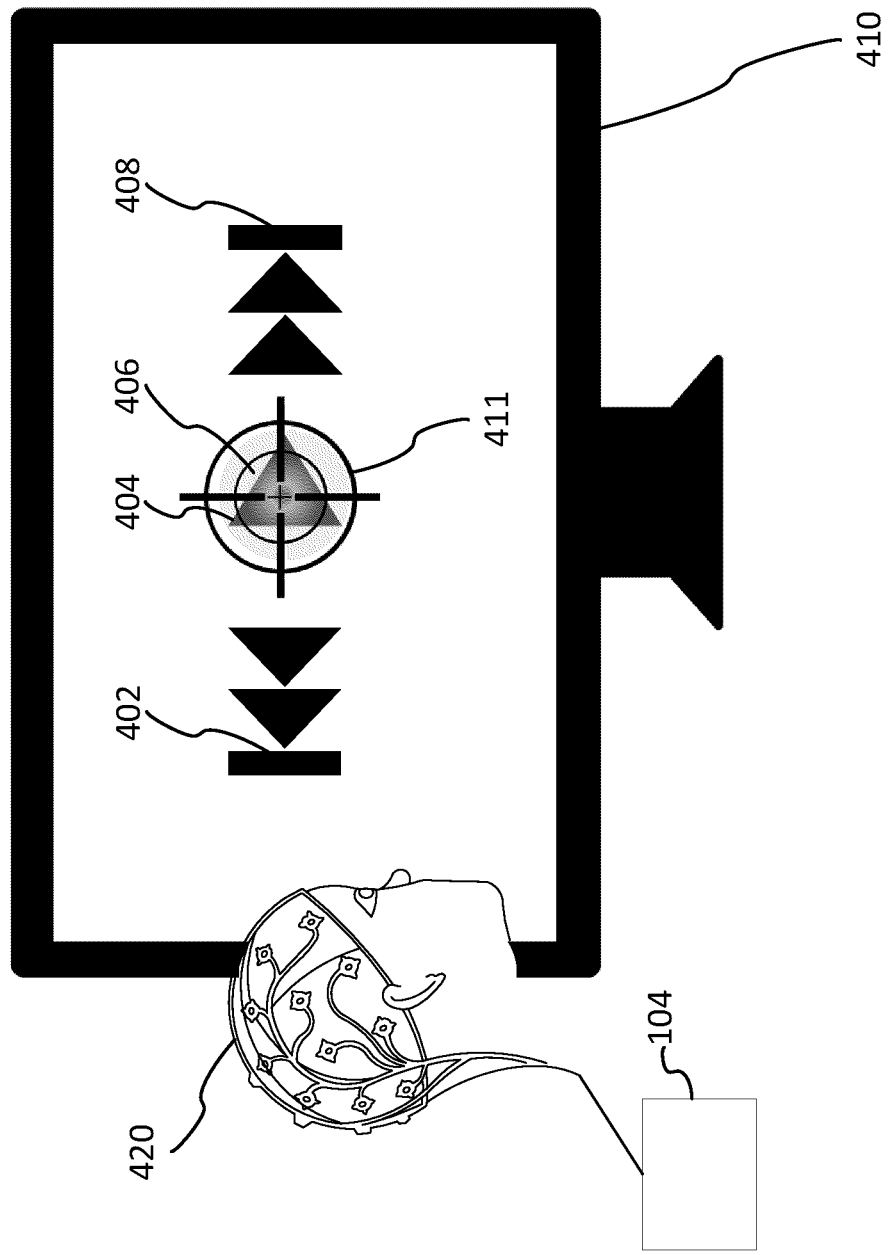
FIG. 4 illustrates an exemplary embodiment of the presentation of a visual feedback by the BCI system of the present disclosure.

FIG. 4 illustrates the user experience of a display device 410 displaying an overlay object 406 with a varying temporal characteristic distinct over a target object 404 (that has been determined to be the object having the current focus of attention). This may provide a retrospective feedback to the user, validating their selection. As illustrated in FIG. 4, the user may conveniently be presented with visual feedback on the display screen 410, so that they are aware that the target object 404 is determined to be the current focus of attention. For example, the display device may display an icon, cursor, or other graphical object or effect (in FIG. 4, a crosshair 411) in close proximity to the target object 404, highlighting (e.g. overlaying) the object that appears to be the current focus of visual attention. This provides a positive feedback loop (where the apparent target object is confirmed (i.e. validated) as the intended target object by virtue of prolonged amplified attention.

In certain embodiments, the visual feedback is "prospective" in that the visual feedback is actively driven to change in appearance. As for the retrospective feedback of FIG. 4, neural responses to objects in a user's field of view in the prospective feedback case are captured by a neural signal capture device in the BCI. The user's neural response to the viewed objects may in turn be measured and decoded to determine which object of interest is the focus of the user's attention and the current level of attention the user is giving to that object, the neural response being stronger when attention is concentrated upon the visual stimulus.

Figure 5:
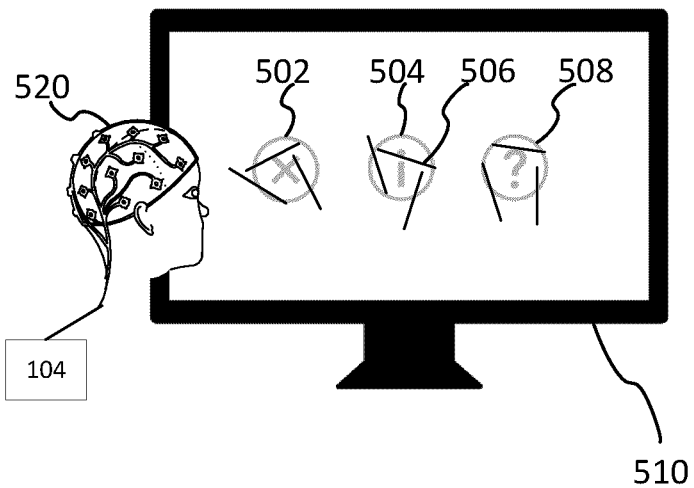
FIG. 5 illustrates an exemplary embodiment of the presentation of a dynamic visual feedback by the BCI system of the present disclosure.
Figure 5:
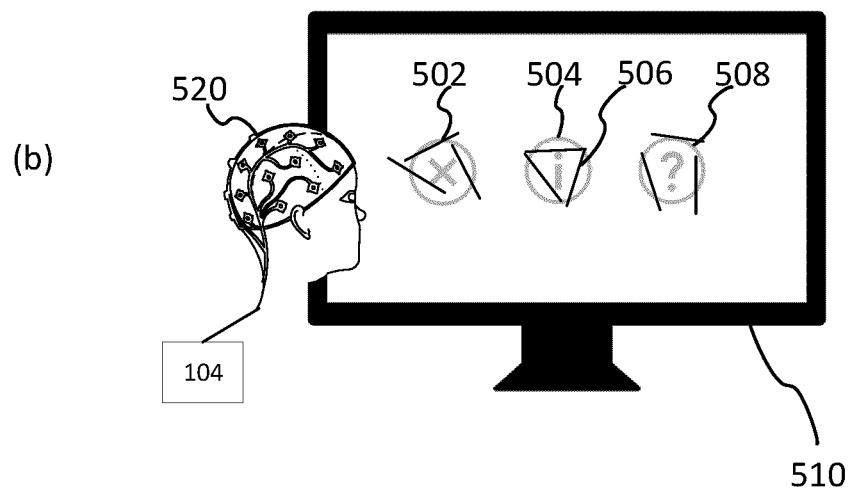
Figure 5:
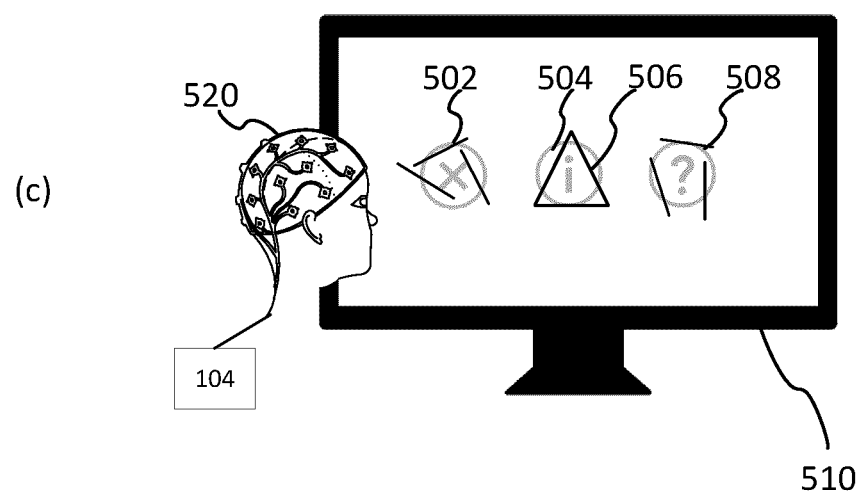

FIG. 5 illustrates stages in the change of appearance of a visual feedback effect. In this exemplary embodiment the target object 504 itself is displayed as a graphical object with a varying temporal characteristic distinct from the temporal characteristic of other displayed objects 502, 506 and/or the background in the display. As previously discussed, apparent target objects are determined based on closest correlation between visual stimulus and decoded neural response. A metric of this correlation may be termed a "decoding score". Candidate target objects are presented with a dynamic visual feedback element (such as an icon, cursor, crosshair or other graphical object) in the display screen: the dynamic visual feedback element varies (e.g. moves or changes color, shape, size, or other visual appearance) as a function of the decoding score. Thus, as may be seen in view (a) of FIG. 5, a dynamic feedback element is present for more than one candidate target object (or indeed for all objects).

The variation of the feedback element is arranged to be linked to the strength of response. Thus, the feedback element of the visual stimulus may change visual form (so that the user sees an effect upon the feedback element that corresponds to their attention level). Viewing the altering appearance of the feedback element, the user is encouraged to pay further attention. Furthermore, the user is provided with a target for that attention and may adapt their behavior to enhance the visual effect (effectively learning how to operate the BCI more efficiently). In other words, the user sees an effect upon the feedback element that they are causing via the BCI and may learn to focus attention using the BCI by seeking to observe the effect alter. For the candidate target objects that are not the focus of attention, the displayed dynamic feedback element will continue to exhibit a substantially unchanged visual form.

In certain embodiments, the feedback element represents degree of attention from absence of attention to a focused level of attention as progressive step-wise or continuous changes between an orderless (e.g. pseudo-random) distribution of visual elements to a completely ordered distribution (e.g. to a recognizable shape, character or symbol such as a reticule, target mark or cross-hair). The feedback element for candidate target objects that are not the focus of attention remains in an orderless state.

In certain embodiments, such as the exemplary embodiment illustrating prospective feedback shown in FIG. 5, each of a plurality of objects in the user's field of view is arranged to exhibit a respective small feedback stimulus (e.g., three separated thin lines moving pseudo-randomly). When the user is paying specific attention to one of the objects (e.g. the "i" icon 504), the three lines superimposed on the icon move towards each other as a function of decoding score until they form a triangle. In this exemplary embodiment, fully pseudo-random lines (as shown at view (a)) mean no decoding at all (for any of the objects), partial decoding for the target object as shown at view (b)) and a full triangle as shown at view (c)) means 100% decoding at the target object. This whole process is observed to be rapid, taking an experienced user less than a second to drive attention from little or no decoding to fully decoded state (e.g. from (a), to (b) and then to (c)). Clearly, the visual display of such feedback has a reflexive cognitive effect on the perception of the target object, amplifying the brain response.

Figure 6:
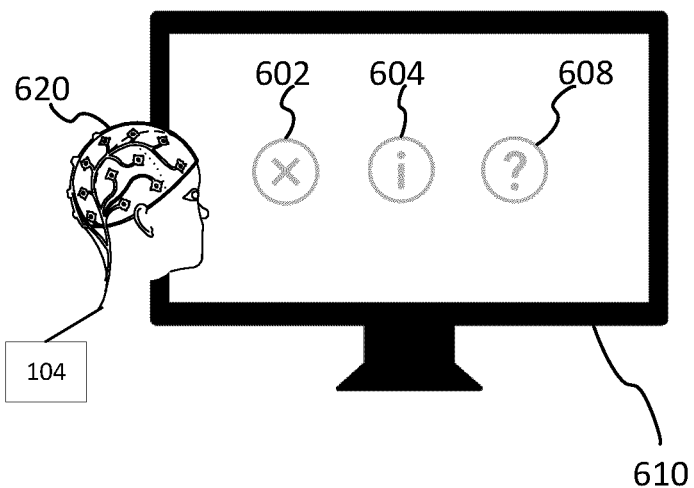
FIG. 6 illustrates a further exemplary embodiment of the presentation of a dynamic visual feedback by the BCI system of the present disclosure.
Figure 6:
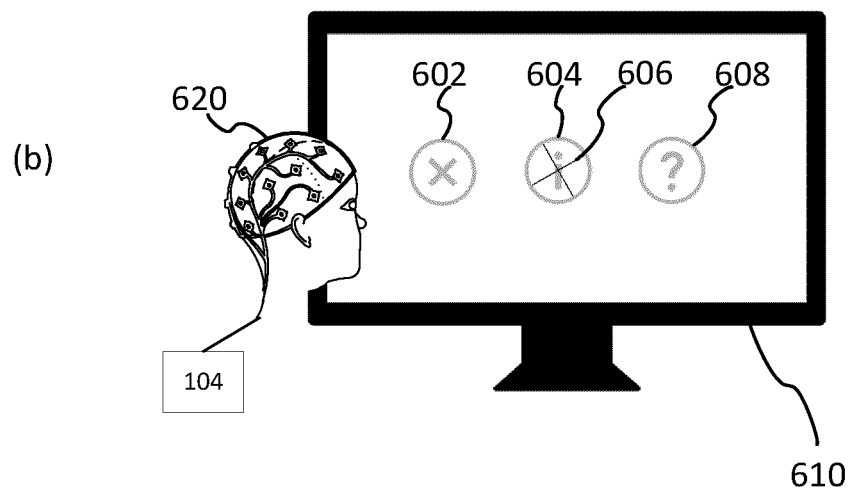
Figure 6:
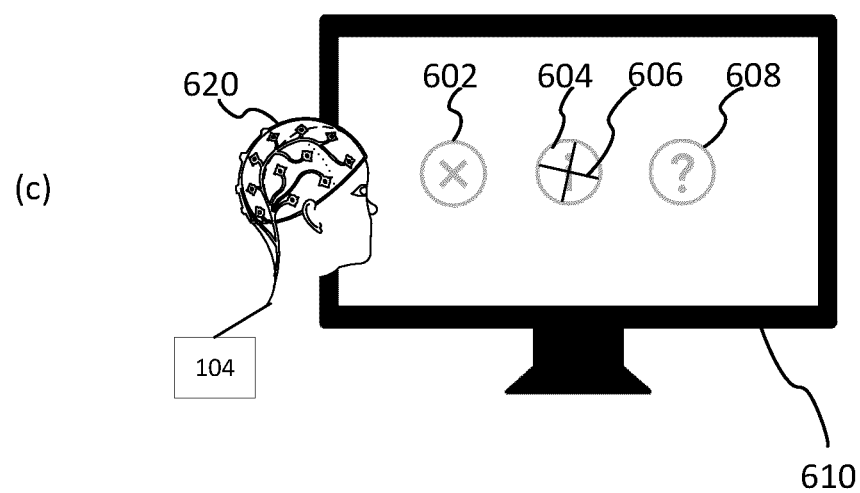

In certain alternative embodiments exhibiting prospective feedback, such as that illustrated in FIG. 6, the visual feedback 606 represents the decoding score by decreasing the transparency, altering the line width, etc. of an overlay object. Thus, in view (a), the visual feedback 606 is essentially invisible; in view (b) the visual feedback 606 is represented by intersecting dashed lines, showing partial decoding; and in view (c), the visual feedback 606, represented by thicker, intersecting, unbroken lines, indicates substantially full decoding.

Active feedback then contrasts with known feedback systems, where a valid selection event requires the user to pay attention to a specific object for more than a predetermined period, with a level of neural response exceeding a predetermined threshold. Using active feedback (and feedback stimuli), it is possible to compute and provide neurofeedback on a shorter timescale (e.g. of the order of seconds), providing information about the intermediate steps ranging from 0% to 100% certainty of a match between neural response and the selected object.

In certain embodiments, the relationship between the feedback stimulus and the decoding performance is linear. In other embodiments, the relationship is not linear: examples of alternative, non-linear, relationships make use of functions such as sigmoid, hyperbolic tangent, Rectified Linear Unit (ReLU), etc. In certain embodiments, the use of a non-linear relationship appears to improve the feedback relationship, particularly at lower levels of certainty, where otherwise the feedback would reflect stochastic/random fluctuations in the EEG signals.

In certain embodiments, the entire visual stimulus is a feedback element. In other embodiments the visual stimulus further includes a background element in addition to the feedback element. In certain embodiments, the background element has the characteristic modulation of the visual stimulus, while the feedback element is not modulated. In certain embodiments, the feedback element has the characteristic modulation of the visual stimulus, while the background element is not modulated.

In certain embodiments, the characteristic modulation of the visual stimulus is applied to both background and feedback element. The magnitude of the modulation in background and feedback element may differ.

In certain embodiments, operation of the BCI may include a brief, initialization and calibration phase. As users may differ markedly in terms of their baseline neural responses to identical stimuli (in particular those having an impaired or damaged visual cortex), the calibration phase may be used to generate a user-specific model of stimulus reconstruction. Such a phase may take less than a minute to construct (typically, ~30 s).

It has been found that objects of focus, in the foveal vision area, are associated with a high degree of HSF signal components. Similarly, it has been found that objects in the peripheral vision area are associated with a high degree of LSF signal components.

By enhancing those differences in HSF and LSF signal components through various filtering methods one can improve the accuracy and speed of BCIs.

In another aspect of the present disclosure, the modulation may be applied preferentially or exclusively to a high spatial frequency component of the projected overlay image (i.e. the background and/or feedback element). Determination of the object of focus of the user may then follow the approach outlined above.

FIG. 3A illustrates the effects of peripheral vision. A subject 305 is shown viewing a display screen 302 displaying a plurality of digits 310, 312 in a keyboard. When the subject tries to focus on digit "5" 310 in the on-screen keypad discussed above, the other (i.e., peripheral) digits (such as "3", 312) act as distractors, drawing the user's attention momentarily, and induce interference in the user's visual system. This interference in turn impedes the performance of the BCI. Consequently, there is a need for an improved method for differentiating between screen targets and their display stimuli in order to determine which one a user is focusing on and for discriminating the object of focus (the target) from the objects peripheral to the target (the distractors) with speed and accuracy.

Figure 9:
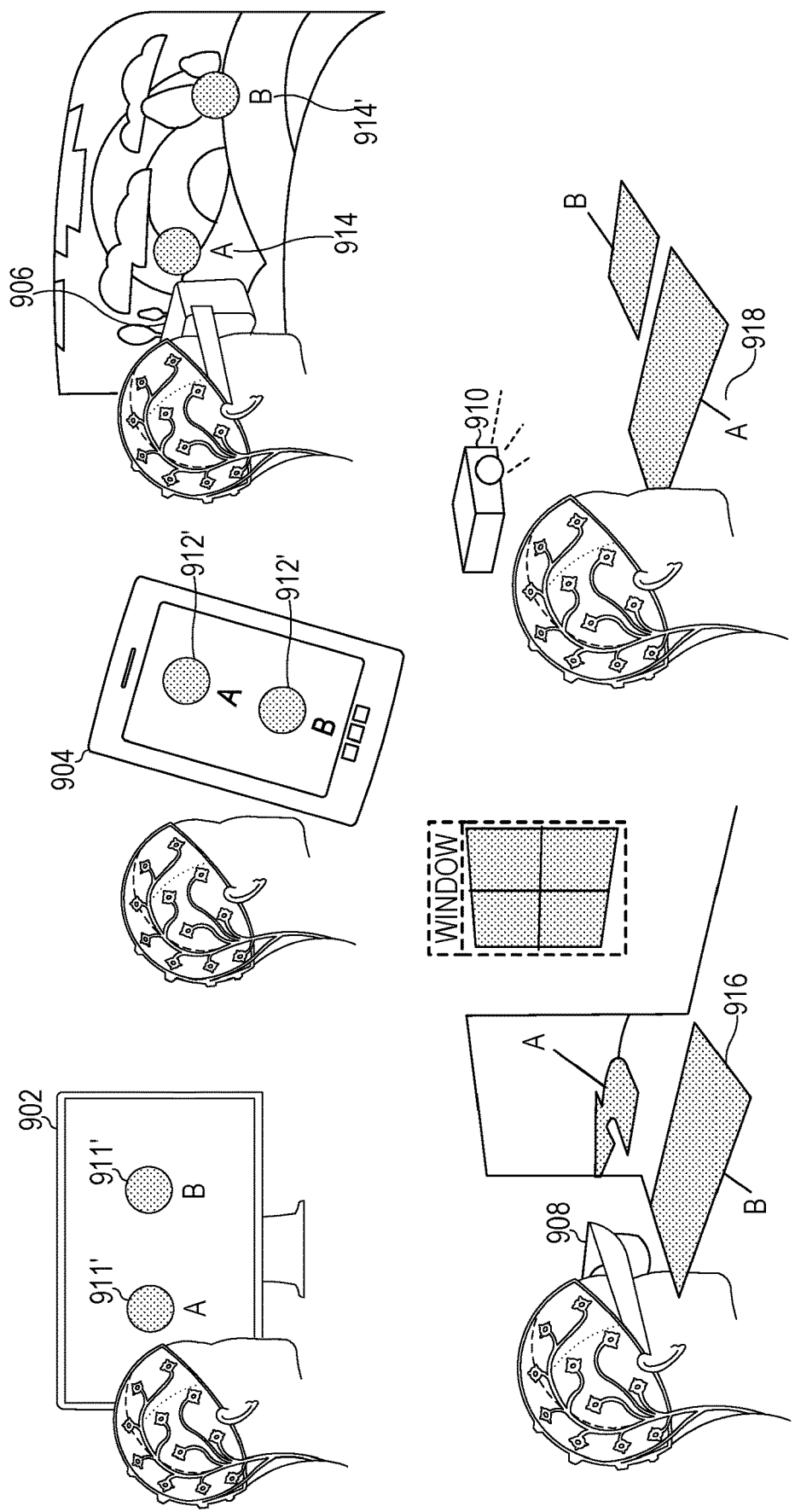
FIG. 9 illustrates various examples of display device suitable for use with the BCI system of the present disclosure.

Conventionally, visual stimuli would take up a significant amount of screen surface, filled with either high energy uniform light (bright white shapes) or coarse checkerboards. These large surfaces would remain dedicated to the visual BCI system and cannot be used for any other purposes than the visual stimulation. These large stimulation surfaces are inconsistent with a fine and discrete integration of the visual BCI system and place limitations in design freedom for user interfaces in display devices, such as those illustrated in FIG. 9.

FIG. 3B illustrates the use of a neural response device such as that in FIGS. 1 and 2 in discriminating between a plurality of target objects. The neural response device worn by the user (i.e. viewer) 305, in FIG. 3B is an electrode helmet for an EEG device. Here, the user wearing the helmet, views a screen 302 displaying a plurality of target objects (the digits in an on-screen keypad), which are blinking at distinctly different times, frequencies and duty cycles. The electrode helmet can convey a signal derived from neural activity. Here, the user is focusing on the digit 5, 310, where at time t1 the digit 3, 312, blinks, at time t2 the digit 4, 314, blinks, at time t3 the digit 5, 310', blinks, and at time t4, the digit 6, 316, blinks. The neural activity as conveyed by the helmet signal would be distinctly different at t3 than at the other points in time. That is because the user is focusing on digit 5. 310, which blinks on, 310', at t3. However, to differentiate that signal occurring at t3 with those at the other times, all the objects on the screen must blink at distinctively different times. Thus, the screen would be alive with blinking objects making for an uncomfortable viewing experience.

The system in FIG. 3B could be using a display signal pattern such as the exemplary pattern shown in FIG. 3C where the screen objects will blink at different points in time, with different frequencies and duty cycles.

One approach to the challenge of determining the object of focus (the target) from the objects peripheral to the target (the distractors) with speed and accuracy relies upon characteristics of the human visual system.

Research into the way in which the human visual sensing operates has shown that, when peering at a screen with multiple objects and focusing on one of those objects, the human visual system will be receptive to both high spatial frequencies (HSF) and low spatial frequencies (LSF). Evidence shows that the human visual system is primarily sensitive to the HSF components of the specific display area being focused on (e.g. the object the user is staring at): this corresponds to the central area in the retina of the subject that is packed with cone cells, known as the fovea centralis. This may be seen in the right-hand view of FIG. 3A where the foveal area of the display 318, where vision is sharpest, is contrasted with the peripheral area 304.

For peripheral objects, conversely, the human visual system is primarily sensitive to their LSF components.

In prior art neural capture systems, thanks to the operation of the human visual system, the neural signals picked up will essentially be impacted by both the HSF components from the target under focus and the LSF components from the peripheral targets. However, since all objects evoke some proportion of both HSF and LSF, processing the neural signals to determine the focus object can be impeded by the LSF noise contributed by peripheral objects. This tends to make identifying the object of focus less accurate and less timely.

The underlying science for this approach relates to the difference in how our eye-brain system processes stimuli from objects of focus and peripheral objects. This dissociation between foveal (center of vision field) and peripheral vision is described in the literature in terms of special frequency channels from the retina to the visual cortex, in which foveal vision is primarily driven by HSF channels conveying visual details while peripheral vision is primarily driven by LSF channels conveying rough visual information such as the global shape of objects without details. These two types of information have been associated with separate neural pathways, distinct functional and different impacts on unconscious and conscious perception.

Spatial frequencies are usually computed in terms of cycles per degree. It mainly depends on three parameters: the density pixel per inch (dpi) also known as pixel per inch (ppi), the distance between user's eyes and monitor, and the cutoff frequency of the spatial filter. Spatial frequency filters can be used such that stimuli signals retain only HSF characteristics, or conversely only LSF characteristics. Spatial frequency filters used in the context of a visual BCI may conveniently perform high-pass filtering for values with over 7 cycles per degree and low-pass filtering for values below 3 cycles per degree. In certain cases, lower threshold values for the low pass filter may in some cases result in the output of a uniform flat tint (such "low pass filters" are still valid filters). By contrast, the maximum value for a high pass filter threshold is limited by either the display system's resolution, and ultimately, the subject's visual physiological capabilities. In any case, the present disclosure operates regardless of the low pass and high pass further thresholds, being agnostic to the specific values of frequency filter and/or transform. The main principle is to dissociate spatial frequency components to optimize a visual BCI.

The human visual system is tuned to process multiple stimuli in parallel at different locations of the visual field, typically unconsciously or subliminally. Consequently, peripheral object stimuli will continue triggering neural responses in the users' brains, even if they appear in the periphery of the visual field. As a result, this poses competition among multiple stimuli and renders the specific neural decoding of the object of focus (the target) more difficult.

Considering again the on-screen keypad of FIG. 3B, the blinking peripheral signals, 312, 314, 316, would evoke LSF neural activity in the viewer that would be captured and processed in parallel with signals evoking HSF neural activity in the viewer stimulated by the blinking digit 5, 310. These peripheral objects, therefore, could be considered distractors and the LSF signals they evoke can be considered noise. One result of this noise is that it takes longer for a system to accurately determine the object of focus.

In one approach of the present disclosure, a plurality of objects is displayed in such a way that each one is separated into a version composed only of the LSF components of the object and a version composed of only HSF components. In one example, the blinking visual stimulus used to elicit a decodable neural response (e.g. SSVEPs) is conveyed only through the HSF version of the object. This blinking HSF version is superimposed on the LSF version (which does not blink). This approach is discussed at greater depth in relation to FIGS. 8A and 8B below.

In each of the feedback overlay arrangements above, the modulation may be applied preferentially or exclusively to a high spatial frequency component of the projected overlay image (i.e. the background and/or feedback element). Preferential modulation of HSF components of overlay objects, target objects and/or visual feedback elements may be used to improve the accuracy of determinations of objects of focus (and to reduce distraction effects).

The BCI described above may be used in conjunction with real world objects, rendering the objects controllable or otherwise subject to interaction. In certain embodiments, the generation of stimuli is handled by one or more light source (such as a light emitting diode, LED) provided in association with (or even, on the surface of) the controllable object.

In certain embodiments, the generation of stimuli is handled by a projector or a scanning laser device so that visual stimuli are projected onto the controllable object and the controllable object outputs a visual stimulus by reflecting a projected stimulus.

As was the case in the BCI using a display screen through which the user interacts with on-screen objects, the controllable objects in the present disclosure can be made to exhibit visual stimuli with characteristic modulations (e.g. blinking stimuli) so that the neural response to the presence of those stimuli become evident and decodable from neural signals captured by a neural signal capture device (such as an EEG device).

In certain embodiments, the determination of focus of attention upon a visual display of a controllable device is used to address a command to that controllable object. The controllable object may then implement an action based on said command: for example, the controllable object may emit an audible sound, unlock a door, switch on or off, change an operational state, etc. The action may also provide the user with visual or other feedback associated with the controllable object: this may be used in conjunction with the positive feedback loop discussed above but may also provide a real-time indication of the valid selection of an operation associated with the controllable object.

Figure 7:
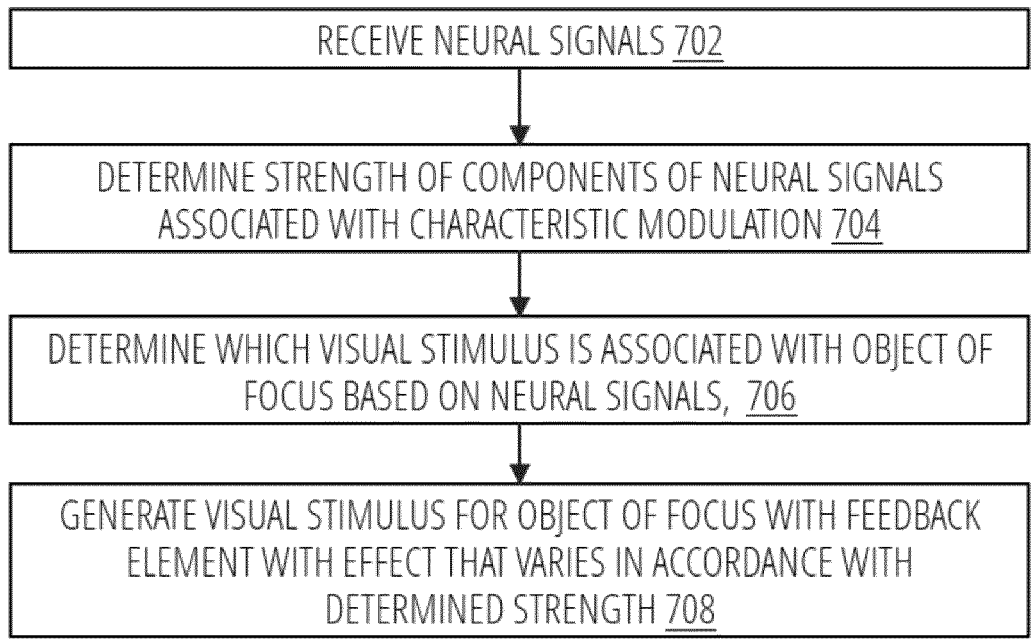
FIG. 7 illustrates the main functional blocks in the method of operation of the BCI in accordance with the present disclosure.

FIG. 7 illustrates the main functional blocks in the method of operation of a BCI system (for example, the BCI system illustrated in FIG. 2) in accordance with the present disclosure. The brain computer interface system includes a display unit, a stimulus generator and a neural signal capture device. The display unit displays image data including at least one object and outputs a visual stimulus to correspond to one or more of said objects, the visual stimulus having a characteristic modulation.

In block 702, a hardware interfacing device (operatively coupled to the neural signal capture device and the stimulus generator), such as interface device 208, receives neural signals from the neural signal capture device.

In block 704, the interfacing device determines a strength of components of the neural signals having a property associated with the respective characteristic modulations of the or each visual stimulus.

In block 706, the interfacing device determines which of the at least one visual stimuli is associated with an object of focus of the user based on the neural signals, the object of focus being inferred from the presence and/or relative strength of the components of the neural signals having a property associated with the characteristic modulation of the visual stimulus.

In block 708, the interfacing device causes the stimulus generator to generate the visual stimulus for the object of focus with a feedback element, the feedback element being displayed with an effect that varies in accordance with the determined strength of the component having a property associated with the characteristic modulations of the visual stimulus for the object of focus.

The active feedback of the present disclosure is associated with several benefits in terms of the user experience (UX) and neural decoding. The feedback stimulus presents the user with a convenient guide to their attention (i.e. an "attention grabber") at a specific location in the display screen, helping them remain focused on the object. For viewers having certain attention-related conditions and mild visual impairments, it has been observed that the presence of such feature assists the user in maintaining focus.

Furthermore, the user is given a task (i.e. causing the feedback stimulus to approach a fully decoded state, indicating "validation" of a selection). This too helps the user to attend to particular objects while suppressing peripheral distractors.

As the user is more focused using such feedback stimuli, it is observed that the user-specific model of stimulus reconstruction built in the initial or calibration phase of operation of the BCI is more accurate while being constructed more rapidly.

In subsequent operational phases, the use of feedback stimuli as described above leads to improved accuracy and speed increases for the real-time BCI applications.

Figure 8A:
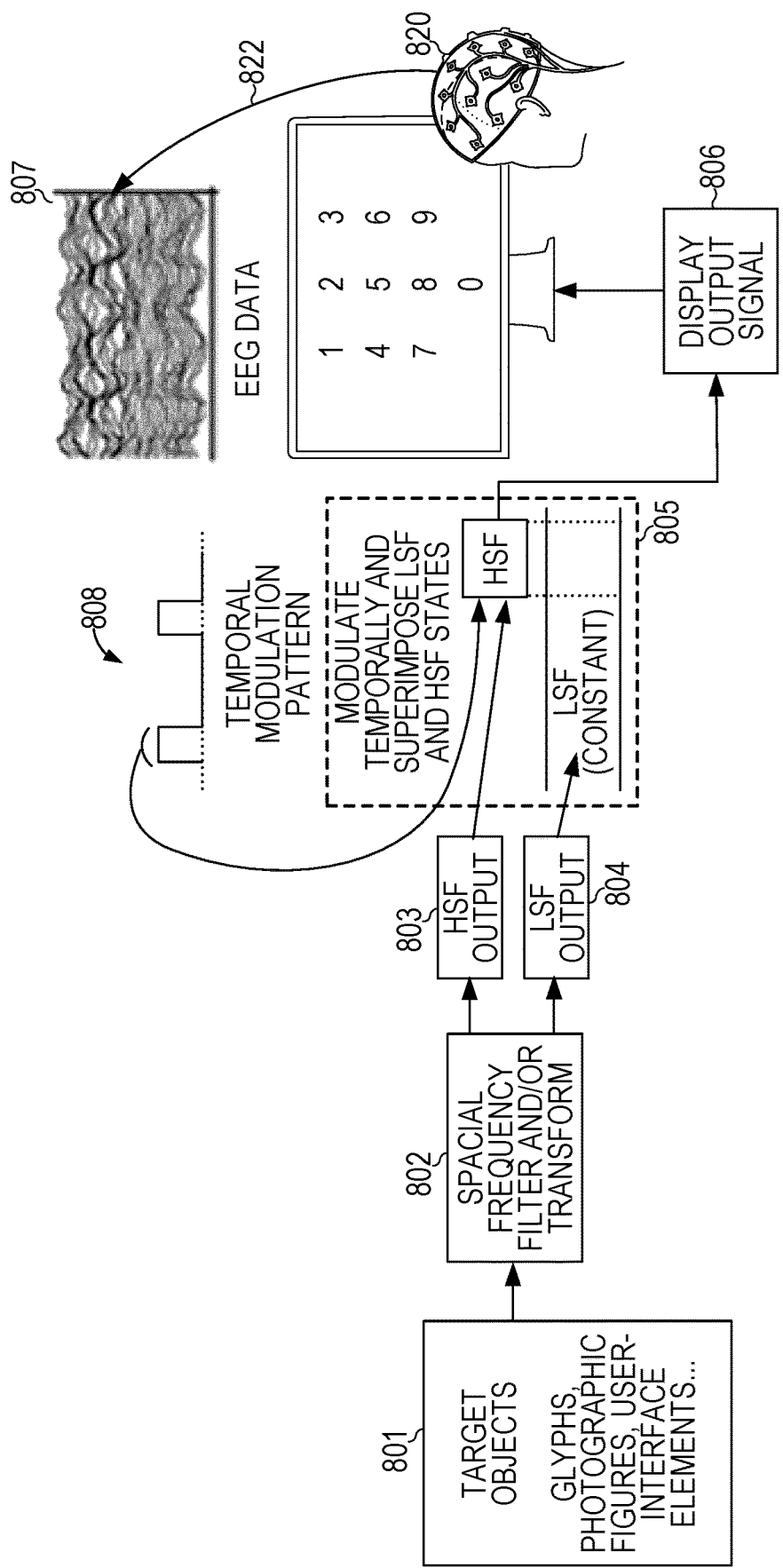
FIGS. 8A and 8B illustrate exemplary arrangements in which HSF versions of either screen objects or overlay objects are modulated.

FIG. 8A is an exemplary illustration of one embodiment of the disclosed subject matter. Here, all target objects 601 are filtered to create HSF and LSF versions of themselves.

In the FIG. 8A embodiment, target objects 801 are distinct graphical elements within a graphical interface presented on a display of a display device. Examples of target objects include glyphs, photographic images, and user-interface elements. The display device may include a processing unit (not shown), a modulator subsystem 805 and a display driver subsystem 806.

For each target object 801, the processing unit of the display device operates to apply a spatial frequency filter 802 (or a spatial frequency transform) to generate HSF and LSF versions (denoted 803 and 804 respectively) of the target object 801. In other embodiments, the target objects 801 may be filtered to create only an HSF version of each object. Thus, only an HSF version is generated.

The modulator subsystem 805 processes and conveys HSF and LSF versions 803, 804 of each object to the display driver subsystem 806. The HSF and LSF versions 803, 804 of each object are processed differently: LSF version signals 804 are encoded to produce a static (e.g. non-blinking) display, whereas the HSF version signals 803 are temporally modulated (e.g. made to blink at distinct times with optionally different frequency and/or duty cycle characteristics). Temporal modulation effects are typically periodic alterations in a visual characteristic of the object such as the luminosity, hue, color component, etc. and may be abrupt (switching between ON and OFF states) or may include more gradual transitions. Examples of temporal modulations include a blinking effect where the brightness characteristics of groups of pixels in the target object are switched between two distinguishable brightness levels. Conveniently the modulation effects encode an optical characteristic to which a user's brain responds (when the object is viewed) in a detectable and decodable manner. The processing may further include increasing contrast levels within the HSF version signals and/or reducing contrast levels in the LSF version signals.

In certain embodiments, the modulation effects may be random or pseudo-random in nature: alterations in a visual characteristic of the object, such as blinking, are performed at random times, e.g. following a pseudo-random temporal pattern. Conveniently, pseudo-random temporal patterns are used, rather than strictly random patterns, to reduce temporal overlap between distinct temporal patterns associated with respective different objects.

The display driver subsystem 806 receives processed HSF and LSF versions of each object from the modulator subsystem 805 (either as separate signals or as a superimposed signal combining modulated HSF and LSF versions). As a result, the signal driving the display includes screen objects where LSF-related signals produce constant display and HSF-related signals produce blinking effects (or other temporal modulation effects).

In certain embodiments, as noted above, the modulator subsystem 805 may process and convey only the HSF version of each object to the display driver subsystem 806: so that only an HSF version is received at the display driver subsystem 806. In such cases, the modulator subsystem 805 applies a high pass filter to generate only the HSF version of each object. In certain other embodiments, the modulator subsystem may apply one or more spatial frequency filters (or spatial frequency transforms) to generate both HSF and LSF versions of the target object but convey only the HSF version of each object to the display driver subsystem 806. In each case, the HSF version is temporally modulated as described above so that the display driver subsystem drives the display with a signal that includes screen objects having HSF components that are temporally modulated. In another embodiment, the display driver subsystem 606 displays the generated HSF version 603 in addition to the (whole) target object 601. In such cases, the contrast in the modulated HSF version may be increased to improve visibility of the visual stimulus over objects of focus.

User attention on the displayed (HSF modulated) object can then be detected (through capture 822 and decoding of neural responses, 807). As a result, the effect of temporal modulation of peripherally viewed objects is significantly reduced. When the user (i.e. subject) wearing a neural response device 820 of the type described in the discussion of FIGS. 1 and 2 above views the screen, only the object of focus will be vibrantly blinking whereas peripheral objects, which are also temporally modulated, will contribute far less noise (since their modulation is only exhibited in HSF components that are out of field for the user intent on the object of focus). That allows the system to determine both quickly and accurately which object the viewer is currently focusing on. Modulated HSF components, being close to invisible when not the object of focus, allow the stimuli to be barely visible to external viewers (i.e. viewers other than the subject), especially when seen from a distance (e.g. a distance greater than twice the distance between a typical active user and the display device. This allows for a discreet (e.g. more private) interaction between the user and the object(s) of focus. This privacy effect is particularly pronounced when the feedback stimulus is made of HSF signals alone.

In certain alternative embodiments, target objects (or "screen objects") are distinct graphical elements presented on a display of a display device, and overlay objects are generated to correspond to one or more of the screen objects. It is the overlay objects, rather than the screen objects themselves, which are now filtered to produce HSF and LSF versions.

Figure 8B:
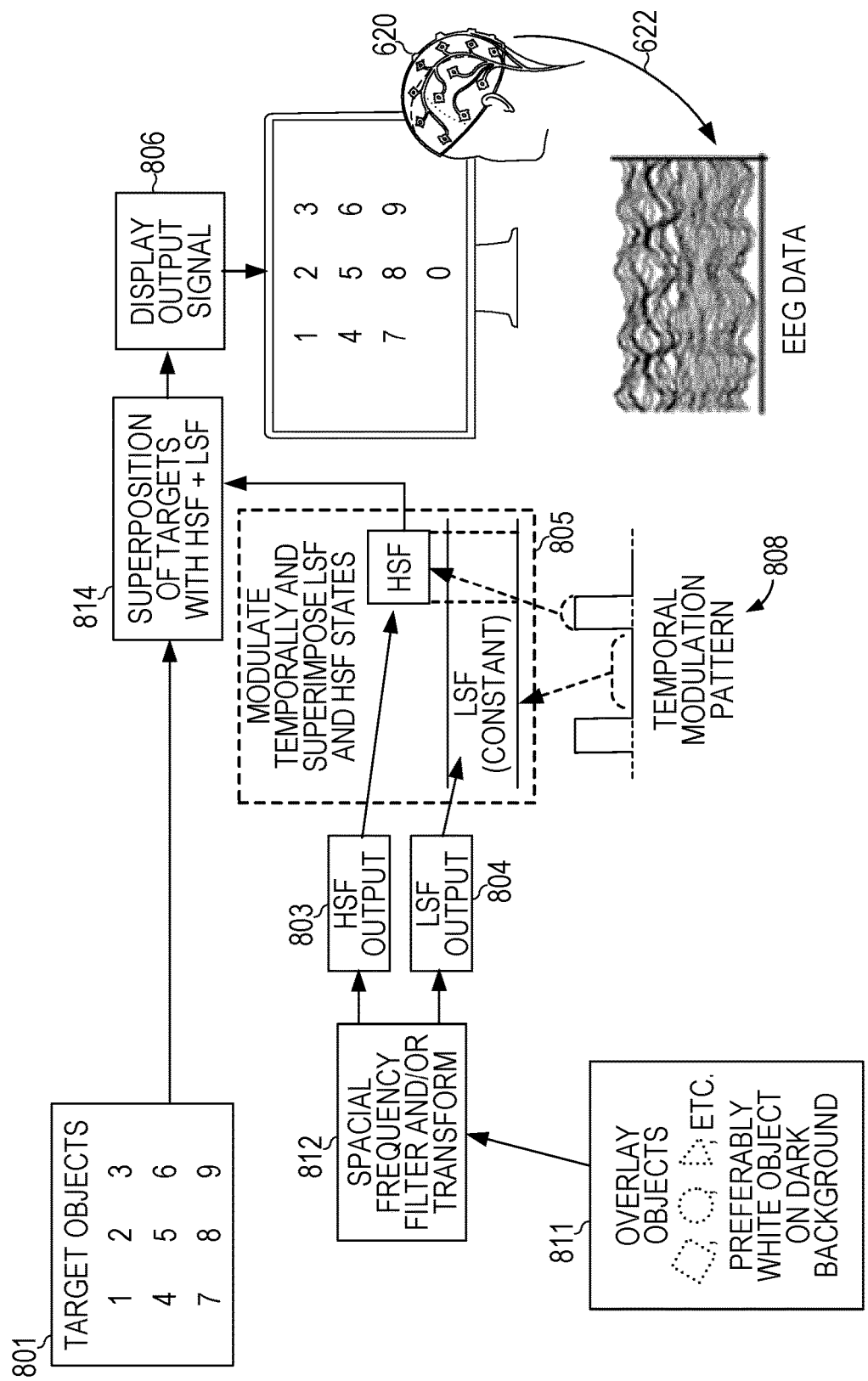

FIG. 8B is an exemplary illustration of another embodiment of the disclosed subject matter implementing such a scheme. As in FIG. 8A, the display device may include a processing unit (not shown), a modulator subsystem 805 and a display driver subsystem 806: the display device of FIG. 8B is further provided with an overlay subsystem 814.

Here, the screen objects 801 will have display signals conveyed to the overlay subsystem 814.

In certain embodiments, each screen object will have associated with it an overlay object. Alternatively, as illustrated in FIG. 8B, only certain screen objects have an associated overlay object 811. A graphical overlay object may, for example, be a geometric shape that surrounds a corresponding screen object.

In certain embodiments, such as that illustrated in FIG. 8B, the overlay objects 811, rather than the screen objects themselves, are now filtered to produce HSF and LSF versions (again denoted 803 and 804 respectively). For each overlay object 811, the processing unit of the display device operates to apply a spatial frequency filter 812 (or a spatial frequency transform) to generate HSF and LSF versions 803, 804 of the overlay object 811.

The modulator subsystem 805 separately modulates the HSF and LSF versions 803, 804 of each overlay object. The modulator subsystem 805 then conveys the modulated HSF and LSF versions of each overlay object to the overlay superposition subsystem 814. The modulator subsystem 805 may optionally convey the modulated HSF and LSF versions of each overlay object as a single superimposed overlay object or as separate versions.

The overlay superposition subsystem 814, receiving processed graphical overlay objects, processes the screen objects 801 and the modulated overlay objects to generate a superposition display signal from the screen and overlay objects.

The superposition subsystem 814, in turn, conveys the processed superposition display signals to the display driver subsystem 806 to drive the display.

The separate modulation may mirror the different processing of target object versions in FIG. 8A. The modulator subsystem 805 is configured to process the overlay objects 811 such that the LSF versions 804 are static (e.g. constantly displayed) whereas the HSF versions 803 are modulated to produce distinctive blinking patterns for differentiating the overlay objects. When the subject focuses on a screen object 801, they see a blinking overlay object 811 quite distinctly whereas the peripheral screen objects and their blinking HSF overlay objects are naturally subdued by the human vision system. Again, the overlay object 811 associated with the target screen object 801 of focus is readily distinguished from the other overlay objects to enable the system to quickly and accurately determine which screen object the user is focusing on.

The above schemes for either processing the target objects themselves to apply a modulation to the HSF version of that object or processing overlay objects to be visually superposed over target objects to apply a modulation to the HSF version of the overlay object become less effective when the HSF component of the target object/overlay object provides an insufficient stimulation impact. For example, the target object may be visually smooth so that there are not enough sharp edges or patches of high contrast to generate a large HSF component. In such cases, no amount of modulation based on the HSF version of the object will be visually apparent to the viewing subject.

Figure 10:
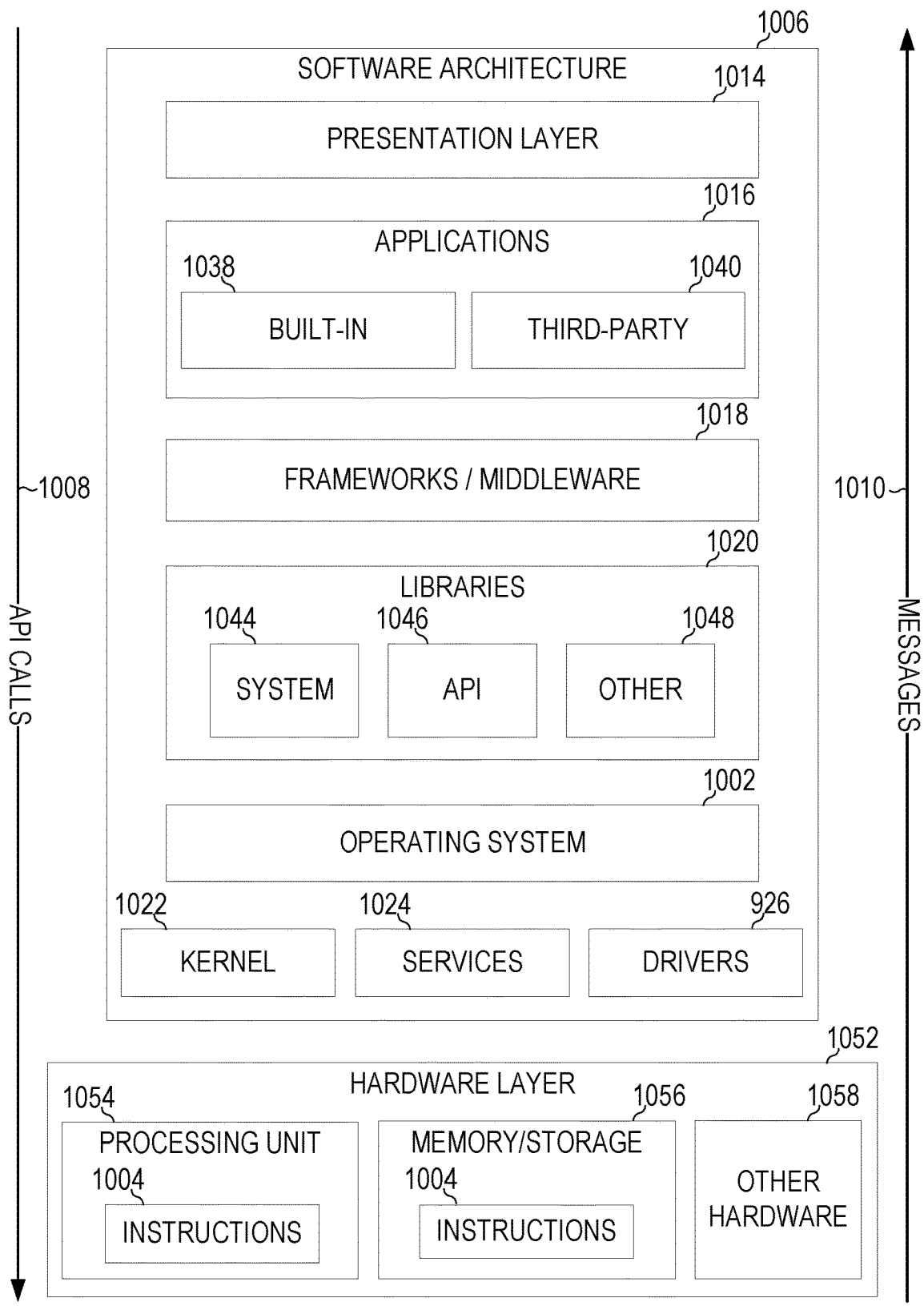
FIG. 10 is block diagram showing a software architecture within which the present disclosure may be implemented, in accordance with some example embodiments.

FIG. 10 is a block diagram illustrating an example software architecture 1006, which may be used in conjunction with various hardware architectures herein described. FIG. 10 is a non-limiting example of a software architecture and it will be appreciated that many other architectures may be implemented to facilitate the functionality described herein. The software architecture 1006 may execute on hardware such as machine 1100 of FIG. 11 that includes, among other things, processors 1104, memory 1106, and input/output (I/O) components 1118. A representative hardware layer 1052 is illustrated and can represent, for example, the machine 1100 of FIG. 11. The representative hardware layer 1052 includes a processing unit 1054 having associated executable instructions 1004. The executable instructions 1004 represent the executable instructions of the software architecture 1006, including implementation of the methods, modules and so forth described herein. The hardware layer 1052 also includes memory and/or storage modules shown as memory/storage 1056, which also have the executable instructions 1004. The hardware layer 1052 may also comprise other hardware 1058, for example dedicated hardware for interfacing with EEG electrodes and/or for interfacing with display devices.

In the example architecture of FIG. 10, the software architecture 1006 may be conceptualized as a stack of layers where each layer provides particular functionality. For example, the software architecture 1006 may include layers such as an operating system 1002, libraries 1020, frameworks or middleware 1018, applications 1016 and a presentation layer 1014. Operationally, the applications 1016 and/or other components within the layers may invoke application programming interface (API) calls 1008 through the software stack and receive a response as messages 1010. The layers illustrated are representative in nature and not all software architectures have all layers. For example, some mobile or special purpose operating systems may not provide the frameworks/middleware 1018, while others may provide such a layer. Other software architectures may include additional or different layers.

The operating system 1002 may manage hardware resources and provide common services. The operating system 1002 may include, for example, a kernel 1022, services 1024, and drivers 1026. The kernel 1022 may act as an abstraction layer between the hardware and the other software layers. For example, the kernel 1022 may be responsible for memory management, processor management (e.g., scheduling), component management, networking, security settings, and so on. The services 1024 may provide other common services for the other software layers. The drivers 1026 may be responsible for controlling or interfacing with the underlying hardware. For instance, the drivers 1026 may include display drivers, EEG device drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1020 may provide a common infrastructure that may be used by the applications 1016 and/or other components and/or layers. The libraries 1020 typically provide functionality that allows other software modules to perform tasks in an easier fashion than by interfacing directly with the underlying operating system 1002 functionality (e.g., kernel 1022, services 1024, and/or drivers 1026). The libraries 1020 may include system libraries 1044 (e.g., C standard library) that may provide functions such as memory allocation functions, string manipulation functions, mathematic functions, and the like. In addition, the libraries 1020 may include API libraries 1046 such as media libraries (e.g., libraries to support presentation and manipulation of various media formats such as MPEG4, H.264, MP3, AAC, AMR, JPG, and PNG), graphics libraries (e.g., an OpenGL framework that may be used to render 2D and 3D graphic content on a display), database libraries (e.g., SQLite that may provide various relational database functions), web libraries (e.g., WebKit that may provide web browsing functionality), and the like. The libraries 1020 may also include a wide variety of other libraries 1048 to provide many other APIs to the applications 1016 and other software components/modules.

The frameworks 1018 (also sometimes referred to as middleware) provide a higher-level common infrastructure that may be used by the applications 1016 and/or other software components/modules. For example, the frameworks/middleware 1018 may provide various graphic user interface (GUI) functions, high-level resource management, high-level location services, and so forth. The frameworks/middleware 1018 may provide a broad spectrum of other APIs that may be used by the applications 1016 and/or other software components/modules, some of which may be specific to a particular operating system or platform.

The applications 1016 include built-in applications 1038 and/or third-party applications 1040.

The applications 1016 may use built-in operating system functions (e.g., kernel 1022, services 1024, and/or drivers 1026), libraries 1020, or frameworks/middleware 1018 to create user interfaces to interact with users of the system. Alternatively, or additionally, in some systems interactions with a user may occur through a presentation layer, such as the presentation layer 1014. In these systems, the application/module "logic" can be separated from the aspects of the application/module that interact with a user.

Figure 11:
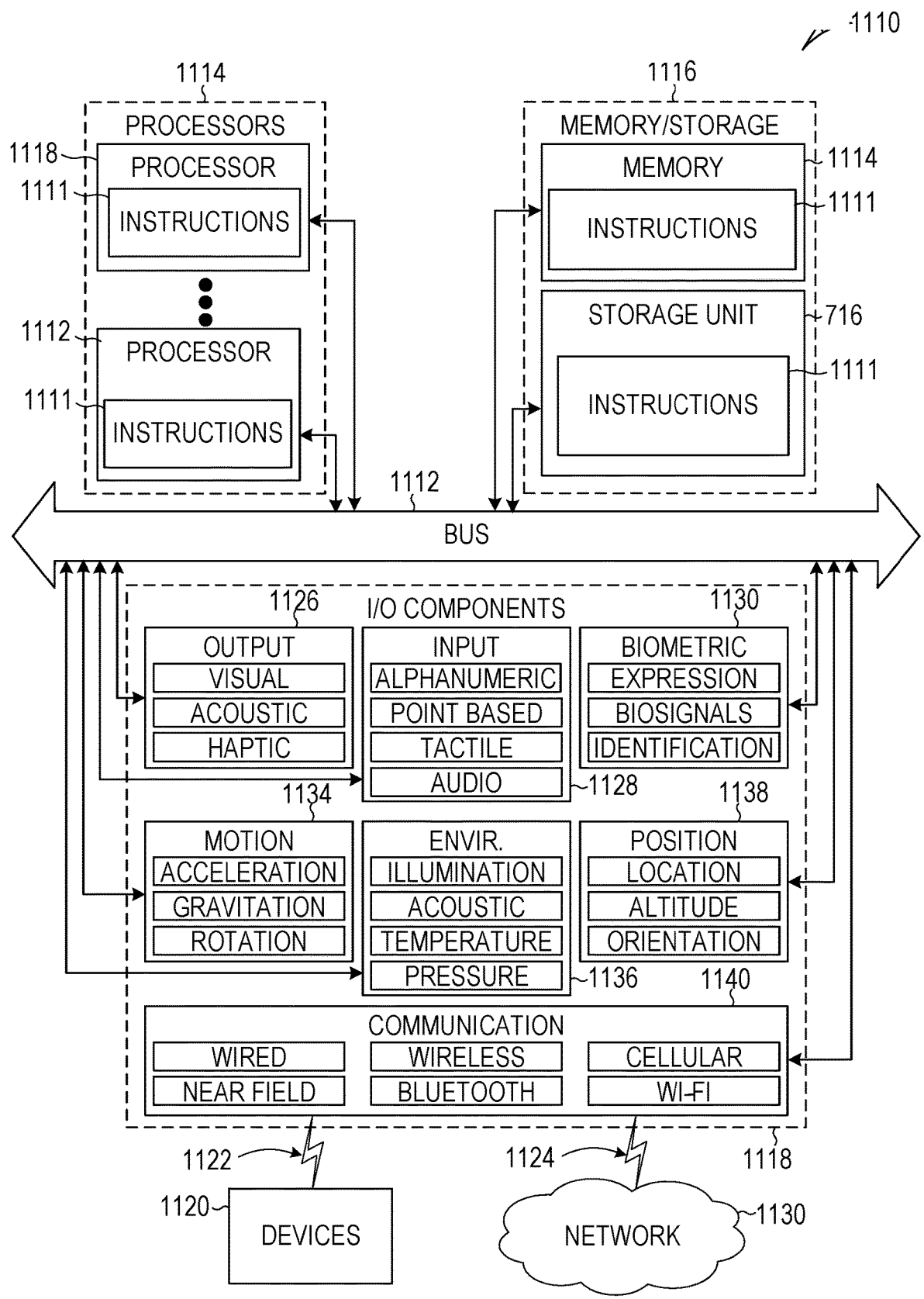
FIG. 11 is a diagrammatic representation of a machine, in the form of a computer system within which a set of instructions may be executed for causing the machine to perform any one or more of the methodologies discussed, in accordance with some example embodiments.

FIG. 11 is a block diagram illustrating components of a machine 1100, according to some example embodiments, able to read instructions from a machine-readable medium (e.g., a machine-readable storage medium) and perform any one or more of the methodologies discussed herein. Specifically, FIG. 11 shows a diagrammatic representation of the machine 1100 in the example form of a computer system, within which instructions 1110 (e.g., software, a program, an application, an applet, an app, or other executable code) for causing the machine 1100 to perform any one or more of the methodologies discussed herein may be executed. As such, the instructions 1110 may be used to implement modules or components described herein. The instructions 1110 transform the general, non-programmed machine 1100 into a particular machine programmed to carry out the described and illustrated functions in the manner described. In alternative embodiments, the machine 1100 operates as a standalone device or may be coupled (e.g., networked) to other machines. In a networked deployment, the machine 1100 may operate in the capacity of a server machine or a client machine in a server-client network environment, or as a peer machine in a peer-to-peer (or distributed) network environment. The machine 1100 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1110, sequentially or otherwise, that specify actions to be taken by the machine 1100. Further, while only a single machine 1100 is illustrated, the term "machine" shall also be taken to include a collection of machines that individually or jointly execute the instructions 1110 to perform any one or more of the methodologies discussed herein.

The machine 1100 may include processors 1104, memory 1106, and input/output (I/O) components 1118, which may be configured to communicate with each other such as via a bus 1102. In an example embodiment, the processors 1104 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 1108 and a processor 1112 that may execute the instructions 1110. The term "processor" is intended to include multi-core processor that may comprise two or more independent processors (sometimes referred to as "cores") that may execute instructions contemporaneously. Although FIG. 11 shows multiple processors, the machine 1100 may include a single processor with a single core, a single processor with multiple cores (e.g., a multi-core processor), multiple processors with a single core, multiple processors with multiples cores, or any combination thereof.

The memory 1106 may include a memory 1114, such as a main memory, a static memory, or other memory storage, and a storage unit 1116, both accessible to the processors 1104 such as via the bus 1102. The storage unit 1116 and memory 1114 store the instructions 1110 embodying any one or more of the methodologies or functions described herein. The instructions 1110 may also reside, completely or partially, within the memory 1114, within the storage unit 1116, within at least one of the processors 1104 (e.g., within the processor's cache memory), or any suitable combination thereof, during execution thereof by the machine 1100. Accordingly, the memory 1114, the storage unit 1116, and the memory of processors 1104 are examples of machine-readable media.

As used herein, "machine-readable medium" means a device able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)), and/or any suitable combination thereof. The term "machine-readable medium" should be taken to include a single medium or multiple media (e.g., a centralized or distributed database, or associated caches and servers) able to store the instructions 1110. The term "machine-readable medium" shall also be taken to include any medium, or combination of multiple media, that is capable of storing instructions (e.g., instructions 1110) for execution by a machine (e.g., machine 1100), such that the instructions, when executed by one or more processors of the machine 1100 (e.g., processors 1104), cause the machine 1100 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The input/output (I/O) components 1118 may include a wide variety of components to receive input, provide output, produce output, transmit information, exchange information, capture measurements, and so on. The specific input/output (I/O) components 1118 that are included in a particular machine will depend on the type of machine. For example, user interface machines and portable machines such as mobile phones will likely include a touch input device or other such input mechanisms, while a headless server machine will likely not include such a touch input device. It will be appreciated that the input/output (I/O) components 1118 may include many other components that are not shown in FIG. 11.

The input/output (I/O) components 1118 are grouped according to functionality merely for simplifying the following discussion and the grouping is in no way limiting. In various example embodiments, the input/output (I/O) components 1118 may include output components 1126 and input components 1128. The output components 1126 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1128 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instruments), tactile input components (e.g., a physical button, a touch screen that provides location and/or force of touches or touch gestures, or other tactile input components), audio input components (e.g., a microphone), and the like.

In further example embodiments, the input/output (I/O) components 1118 may include biometric components 1130, motion components 1134, environment components 1136, or position components 1138 among a wide array of other components. For example, the biometric components 1130 may include components to detect expressions (e.g., hand expressions, facial expressions, vocal expressions, body gestures, or eye tracking), measure biosignals (e.g., blood pressure, heart rate, body temperature, perspiration, or brain waves, such as the output from an EEG device), identify a person (e.g., voice identification, retinal identification, facial identification, fingerprint identification, or electroencephalogram based identification), and the like. The motion components 1134 may include acceleration sensor components (e.g., accelerometer), gravitation sensor components, rotation sensor components (e.g., gyroscope), and so forth. The environmental environment components 1136 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment. The position components 1138 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The input/output (I/O) components 1118 may include communication components 1140 operable to couple the machine 1100 to a network 1132 or devices 1120 via a coupling 1124 and a coupling 1122 respectively. For example, the communication components 1140 may include a network interface component or other suitable device to interface with the network 1132. In further examples, communication components 1140 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1120 may be another machine or any of a wide variety of peripheral devices (e.g., a peripheral device coupled via a Universal Serial Bus (USB)). Where an EEG device or display device is not integral with the machine 1100, the device 1120 may be an EEG device and/or a display device.

Although described through a number of detailed exemplary embodiments, the portable devices for the acquisition of electroencephalographic signals according to the present disclosure comprise various variants, modifications and improvements which will be obvious to those skilled in the art, it being understood that these various variants, modifications and improvements fall within the scope of the subject of the present disclosure, as defined by the following claims.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Thus, the present disclosure describes a system and method for improving the accuracy, speed performance and visual comfort of BCIs.

In accordance with an aspect of the present disclosure the system is a closed-loop system comprising: a display subsystem operative to display one or more object images; a display-driver subsystem operative to convey a display signal to said display subsystem; an HSF/LSF discriminating, filtering and processing subsystem operative to essentially separate said object images into HSF and LSF versions that evoke essentially HSF neural responses and essentially LSF neural responses, respectively; said HSF/LSF discriminating, filtering and processing subsystem operative to process said HSF versions so as to blink on and off, and said LSF versions so as to be non-blinking; and an electrode helmet operative to detect neural brain activity, produce an electrical signal representing said neural brain activity, and to convey said electrical signal to said HSF/LSF discriminating, filtering and processing subsystem wherein said electrical signal is compared to concurrent display signals in said HSF/LSF discriminating, filtering and processing subsystem so as to associate said electrical signal with a corresponding said concurrent display signal.

The system may further comprise said display signal being used to modulate screen objects.

Alternatively or additionally, the system may further comprise said display signal being used to modulate screen object overlays.

In accordance with a further aspect of the present disclosure there is provided a method for improving the accuracy, speed performance and visual comfort of BCIs, the method comprising: detecting neural signals from helmet electrodes when worn on a user's head and while said user gazes at objects on a display screen; correlating said detected neural signals with display signals used to modulate said objects; comparing said neural signals with said display signals; and identifying an object of focus wherein said neural signal and said display signals correlate.

The method may further comprise identifying said object of focus wherein said object of focus is a screen object.

Alternatively or additionally, the method may further comprise identifying said object of focus wherein said object of focus is a screen-object overlay.

Examples

To better illustrate the system and methods disclosed herein, a non-limiting list of examples is provided here:

1. A method comprising:
   filtering graphical data for one or more screen objects, to generate a high spatial frequency, HSF, version of the or each screen object;
   for each HSF version of the screen object, applying a characteristic modulation;
   generating display signals including visual stimuli corresponding to said modulated versions of the screen objects;
   displaying the display signals on a display screen;
   receiving neural signals of a user from a neural signal capture device while said user gazes at the display screen;
   for each visual stimulus, determining whether the neural signals received when the user gazes at the display screen include a neural signature of said visual stimulus; and
   identifying an object of focus of the user in the display signals displayed on the display screen when it is determined that the neural signals include the neural signature of the visual stimulus, the object of focus being a display object on the display screen that coincides with the visual stimulus.

2. The method of example 1, wherein the neural signals correspond to neural oscillations measured in a visual cortex of the user's brain.

3. The method of example 1 or 2, wherein the neural signature comprises information associated with the characteristic modulation of the visual stimulus.

4. The method of any one of examples 1, 2 or 3, further comprising filtering graphical data for one or more screen objects, to generate a low spatial frequency, LSF, version of the or each screen object; and, for each LSF version of the screen object, encoding a static display signal.

5. The method of any one of examples 1-4, wherein the graphical data for the one or more screen objects is filtered using at least one of a spatial frequency filter or a spatial frequency transform.

6. The method of any one of examples 1-5, wherein the characteristic modulation is a characteristic temporal modulation.

7. The method of any one of examples 1-6, wherein determining whether the received neural signals include the digital signature of the visual stimulus includes: performing spectral analysis on the received neural signals, and determining whether the spectral characteristics of the received neural signals correspond to the spectrum associated with the characteristic modulation of the visual stimulus.

8. The method of any one of examples 1-7, wherein the neural signal capture device includes an EEG helmet comprising electrodes, the EEG helmet being configured to be worn on a user's head.

9. The method of any one of examples 1-8, wherein said object of focus is the screen object itself.

10. The method of any one of examples 1-9, wherein said object of focus is a display object displayed on the display screen and the visual stimulus is an overlay object different from the display object and displayed over the display object.

11. A brain computer interface system, comprising:
   a display subsystem configured to present a display screen to a user;

a neural signal capture device configured to capture neural signals associated with the user;

an interfacing device operatively coupled to the display subsystem and the neural signal capture device, the interfacing device including:
  a memory; and
  a processor operatively coupled to the memory and configured:
    to filter graphical data for one or more screen objects, to generate a high spatial frequency, HSF, version of the or each screen object;
    for each HSF version of the screen object, to apply a characteristic modulation;
    to generate display signals including visual stimuli corresponding to said modulated versions of the screen objects;
    to convey the display signals to the display subsystem for display on the display screen;
    to receive neural signals of the user from the neural signal capture device while said user gazes at the display screen;
    for each visual stimulus, to determine whether the neural signals received when the user gazes at the display screen include a neural signature of said visual stimulus; and
    to identify an object of focus of the user in the display signals displayed on the display screen when it is determined that the neural signals include the neural signature of the visual stimulus, the object of focus being a display object on the display screen that coincides with the visual stimulus.

12. The brain computer interface system of example 11, wherein the processor is further configured:
  to associate the object of focus with at least one control item from a set of control items;
  to determine, based on the object of focus and the at least one control item, an action intended by the user; and
  to implement the action intended by the user.

13. The brain computer interface system of example 11 or example 12, wherein the processor further comprises:
  a display-driver subsystem operative to convey a display signal to said display subsystem.

14. The brain computer interface system of any one of examples 11 to 13, wherein the neural signal capture device comprises an electrode helmet operative to detect neural brain activity, produce an electrical signal representing said neural brain activity, and to convey said electrical signal to the interfacing device.

15. The brain computer interface system of any one of examples 11 to 14, wherein the object of focus is the screen object itself.

16. The brain computer interface system of any one of examples 11 to 14, wherein said object of focus is a display object displayed on the display screen and the visual stimulus is an overlay object different from the display object and displayed over the display object.

17. The brain computer interface system of any one of examples 11 to 16, wherein the processor is further configured: to filter graphical data for one or more screen objects to generate a low spatial frequency, LSF, version of the or each screen object; and, for each LSF version of the screen object, to encode a static display signal.

18. A computer-readable storage medium, the computer-readable storage medium carrying instructions that, when executed by a computer, cause the computer to perform operations comprising:

filtering graphical data for one or more screen objects, to generate a high spatial frequency. HSF, version of the or each screen object;

for each HSF version of the screen object, applying a characteristic modulation;

generating display signals including visual stimuli corresponding to said modulated versions of the screen objects;

displaying the display signals on a display screen;

receiving neural signals of a user from a neural signal capture device while said user gazes at the display screen;

for each visual stimulus, determining whether the neural signals received when the user gazes at the display screen include a neural signature of said visual stimulus; and identifying an object of focus of the user in the display signals displayed on the display screen when it is determined that the neural signals include the neural signature of the visual stimulus, the object of focus being a display object on the display screen that coincides with the visual stimulus.

19. The computer-readable storage medium of example 18, wherein the neural signals correspond to neural oscillations measured in a visual cortex of the user's brain.

20. The computer-readable storage medium of example 18 or example 19, wherein the neural signature comprises information associated with the characteristic modulation of the visual stimulus.

21. The computer-readable storage medium of any one of examples 18, 19 or 20, wherein the instructions further cause the computer to perform operations comprising: filtering graphical data for one or more screen objects, to generate a low spatial frequency, LSF, version of the or each screen object; and, for each LSF version of the screen object, encoding a static display signal.

22. The computer-readable storage medium of any one of examples 18 to 21, wherein the graphical data for the one or more screen objects is filtered using at least one of a spatial frequency filter or a spatial frequency transform.

23. The computer-readable storage medium of any one of examples 18 to 22, wherein the characteristic modulation is a characteristic temporal modulation.

24. The computer-readable storage medium of any one of examples 18 to 23, wherein determining whether the received neural signals include the digital signature of the visual stimulus includes: performing spectral analysis on the received neural signals, and determining whether the spectral characteristics of the received neural signals correspond to the spectrum associated with the characteristic modulation of the visual stimulus.

25. A brain computer interface system, comprising:
  a display unit for displaying image data, the image data including at least one object, the display unit further outputting a respective visual stimulus to correspond to one or more of said objects,
  a stimulus generator for generating the or each visual stimulus with a corresponding characteristic modulation;
  a neural signal capture device configured to capture neural signals associated with a user; and
  an interfacing device operatively coupled to the neural signal capture device and the stimulus generator, the interfacing device being configured to:
    receive the neural signals from the neural signal capture device;

determine a strength of components of the neural signals having a property associated with the respective characteristic modulations of the or each visual stimulus;

determine which of the at least one visual stimuli is associated with an object of focus of the user based on the neural signals, the object of focus being inferred from the presence and/or relative strength of the components of the neural signals having a property associated with the characteristic modulation of the visual stimulus; and cause the stimulus generator to generate the visual stimulus for the object of focus with a feedback element, the feedback element being displayed with an effect that varies in accordance with the determined strength of the component having a property associated with the characteristic modulations of the visual stimulus for the object of focus.

26. The system of example 25, wherein the displayed effect of the feedback element varies as a linear function of the strength of response.

27. The system of example 25, wherein the displayed effect of the feedback element varies as a non-linear function of the strength of response.

28. The system of example 27, wherein the non-linear function is selected from a sigmoid function, a Rectified Linear Unit (RELU) function or a hyperbolic tangent function.

29. The system of example 25, wherein the modulation is selectively applied to the high spatial frequency (HSF) component of the visual stimulus.

30. The system of example 25, wherein the displayed effect includes a step-wise or continuous change from an initial visual state to a final visual state.

31. The system of example 25, wherein the visual stimulus is the feedback element.

32. The system of example 25, wherein the visual stimulus further includes a background element in addition to the feedback element.

33. The system of example 32, wherein the background element has the characteristic modulation of the visual stimulus, while the feedback element is not modulated.

34. The system of example 32, wherein the feedback element has the characteristic modulation of the visual stimulus, while the background element is not modulated.

35. The system of example 32, wherein the characteristic modulation of the visual stimulus is applied to both background and feedback element.

36. The system of example 35, wherein the magnitude of the modulation in background and feedback element differs.

37. A method of operation of a brain computer interface system, the brain computer interface system including a display unit, a stimulus generator and a neural signal capture device, the display unit displaying image data including at least one object and outputting a visual stimulus to correspond to one or more of said objects, the visual stimulus having a characteristic modulation, wherein the method comprises, in a hardware interfacing device operatively coupled to the neural signal capture device and the stimulus generator:

receiving the neural signals from the neural signal capture device;

determining a strength of components of the neural signals having a property associated with the respective characteristic modulations of the or each visual stimulus;

determining which of the at least one visual stimuli is associated with an object of focus of the user based on the neural signals, the object of focus being inferred from the presence and/or relative strength of the components of the neural signals having a property associated with the characteristic modulation of the visual stimulus; and causing the stimulus generator to generate the visual stimulus for the object of focus with a feedback element, the feedback element being displayed with an effect that varies in accordance with the determined strength of the component having a property associated with the characteristic modulations of the visual stimulus for the object of focus.

38. The method of example 37, wherein the displayed effect of the feedback element varies as a linear function of the strength of response.

39. The method of example 37, wherein the displayed effect of the feedback element varies as a non-linear function of the strength of response.

40. The method of example 37, wherein the modulation is selectively applied to the high spatial frequency (HSF) component of the visual stimulus.

41. A computer-readable storage medium, the computer-readable storage medium carrying instructions that, when executed by a computer, cause the computer to perform the method of any one of examples 37 to 40.

What is claimed is:

1. A brain computer interface system, comprising:

a display unit for displaying image data, the image data including an object, the display unit further outputting a first respective visual stimulus to correspond to the object;

a stimulus generator for generating the first visual stimulus with a corresponding characteristic modulation;

a neural signal capture device configured to capture neural signals associated with a user; and an interfacing device operatively coupled to the neural signal capture device and the stimulus generator, the interfacing device being configured to:

receive the neural signals from the neural signal capture device;

determine a strength of components of the neural signals having a property associated with the respective characteristic modulation of the first visual stimulus;

determine the object as an object of focus of the user based on the neural signals, the object of focus being inferred from a presence of the components of the neural signals having a property associated with the characteristic modulation of the visual stimulus; and in response to determining the object as the object of focus, cause the stimulus generator to generate a second respective visual stimulus for the object of focus, the second respective visual stimulus including a background element having a low spatial frequency (LSF) that does not exceed 3 cycles per degree and a visual feedback element having a high spatial frequency (HSF) exceeding a threshold of 7 cycles per degree, the visual feedback element being displayed to the user with a visual effect selectively applied to the visual feedback element and not applied to the background element, the visual effect varying in accordance with the strength of the components having a property associated with the characteristic modulations of the first visual stimulus for the object of focus while the background component is not modulated.

2. The brain computer interface system of claim 1, wherein the displayed visual effect of the visual feedback element varies as a linear function of the strength of response.

3. The brain computer interface system of claim 1, wherein the displayed visual effect of the visual feedback element varies as a non-linear function of the strength of response.

4. The brain computer interface system of claim 3, wherein the non-linear function is selected from a sigmoid function, a Rectified Linear Unit (RELU) function or a hyperbolic tangent function.

5. The brain computer interface system of claim 1, wherein the displayed visual effect includes a step-wise or continuous change from an initial visual state to a final visual state.

6. The brain computer interface system of any one of claim 1, wherein the second visual stimulus is the visual feedback element.

7. The brain computer interface system of claim 1, wherein the visual feedback element has the characteristic modulation of the first visual stimulus, while the background element is not modulated.

8. A method of operation of a brain computer interface system, the brain computer interface system including a display unit, a stimulus generator and a neural signal capture device, the method comprising:
displaying, by the display unit, to a user, image data including an object and outputting a first visual stimulus corresponding to the object, the first visual stimulus having a characteristic modulation;
performing, by a hardware interfacing device operatively coupled to the neural signal capture device and the stimulus generator, operations comprising:
receiving neural signals from the neural signal capture device;
determining a strength of components of the neural signals having a property associated with the respective characteristic modulation of the first visual stimulus;
determining the object as an object of focus of the user based on the neural signals, the object of focus being inferred from a presence of the components of the neural signals having a property associated with the characteristic modulation of the visual stimulus; and
in response to determining the object as the object of focus, causing the stimulus generator to generate a second respective visual stimulus for the object of focus, the second respective visual stimulus including a background element having a low spatial frequency (LSF) that does not exceed 3 cycles per degree and a visual feedback element and a visual feedback element having a high spatial frequency (HSF) exceeding a threshold of 7 cycles per degree, the visual feedback element being displayed to the user with a visual effect selectively applied to the visual feedback element and not applied to the background element, the visual effect varying in accordance with the strength of the components having a property associated with the characteristic modulations of the first visual stimulus for the object of focus while the background element is not modulated.

9. The method of claim 8, wherein the displayed visual effect of the visual feedback element varies as a linear function of the strength of response.

10. The method of claim 8, wherein the displayed visual effect of the visual feedback element varies as a non-linear function of the strength of response.

11. A computer-readable storage medium, the computer-readable storage medium storing instructions that, when executed by a computer, cause the computer to perform operations comprising:
displaying to a user, image data including an object and a first visual stimulus corresponding to the object, the first visual stimulus having a characteristic modulation;
receiving neural signals of the user from a neural signal capture device;
determining a strength of components of the neural signals having a property associated with characteristic modulation of the first visual stimulus;
determining the object as an object of focus of the user based on the neural signals, the object of focus being inferred from a presence of the components of the neural signals having a property associated with the characteristic modulation of the visual stimulus; and
in response to determining the object as the object of focus, generating a second respective visual stimulus for the object of focus, the second respective visual stimulus including a background element having a low spatial frequency (LSF) that does not exceed 3 cycles per degree and a visual feedback element having a high spatial frequency (HSF) exceeding a threshold of 7 cycles per degree, the visual feedback element being displayed to the user with a visual effect selectively applied to the visual feedback element and not applied to the background element, the visual effect varying in accordance with the strength of the component having a property associated with the characteristic modulations of the first visual stimulus for the object of focus while the background component is not modulated.

12. The computer-readable storage medium of claim 11, wherein the displayed visual effect of the feedback element varies as a linear function of the strength of response.

13. The computer-readable storage medium of claim 11, wherein the displayed visual effect of the feedback element varies as a non-linear function of the strength of response.

* * * * *